(12) United States Patent
Chatterjee

(10) Patent No.: US 6,713,057 B1
(45) Date of Patent: Mar. 30, 2004

(54) COMPOSITIONS AND METHODS FOR MODULATING SERUM CHOLESTEROL

(75) Inventor: Subroto Chatterjee, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/511,532

(22) Filed: Feb. 23, 2000

Related U.S. Application Data

(60) Provisional application No. 60/121,447, filed on Feb. 24, 1999.

(51) Int. Cl.$^7$ .......................... A61K 38/46; A61K 38/00
(52) U.S. Cl. .......................................... 424/94.6; 514/13
(58) Field of Search ............................ 424/94.6; 514/13

(56) References Cited

U.S. PATENT DOCUMENTS

| | | | |
|---|---|---|---|
| 3,876,789 A | 4/1975 | Santilli et al. | 424/251 |
| 5,498,696 A | 3/1996 | Briggs et al. | 530/350 |
| 5,919,687 A | 7/1999 | Chatterjee | 435/199 |
| 5,972,928 A | 10/1999 | Chatterjee | 514/212 |

FOREIGN PATENT DOCUMENTS

| FR | 2747307 A | 10/1997 |
|---|---|---|

OTHER PUBLICATIONS

Goeddel, D.V., et al., "Tumor Necrosis Factors: Structure And Biological Activities", Cold Spring Harbor Symp. On Quant. Biol., vol. 51: 597–609.*
R. Bittman, et al., "Interaction Of Cholesterol With Sphingomyelin In Monolayers And Vesicles", Biochemistry, vol. 33: 11776–11781 (1994).*
L. Gronberg, et al., "Interaction Of Cholesterol With Sphingomyelin Derivatives In Mixed Monolayers", Biochemistry, vol. 30: 10746–10754 (1991).*
X. Wang, et al., "SREBP–1, A Membrane–Bound Transcription Factor Released By Sterol–Regulated Proteolysis", Cell, vol. 77: 53–62 (1994).*
Adam–Klages, S., et al., "FAN, A Novel WD–Repeat Protein, Couples The p55 TNF–Receptor To Neutral Sphingomyelinase", Cell, vol. 86: 937–947 (1996).*
Brown, M.S., et al., "The SREBP Pathway: Regulation Of Cholesterol Metabolism By Proteolysis Of A Membrane–Bound Transcription Factor", Cell, vol. 89: 331–340 (1997).*
S. Chatterjee, "Neutral Sphingomyelinase Action Stimulates Signal Transduction Of Tumor Necrosis Factor–2 In The Synthesis Of Cholesteryl Esters In Human Fibroblasts", J. Biol. Chem., vol. 269: 879–882 (1994).*
S. Chatterjee, "Neutral Sphingomyelinase Increases The Binding, Internalization, And Degradation Of Low Density Lipoproteins And Synthesis Of Cholesteryl Ester In Cultured Human Fibroblasts", J. Biol. Chem., vol. 268: 3401–3406 (1993).*

Clejan, S., et al., "Decreases In Rates Of Lipid Exchange Between *Mycoplasma gallisepticum* Cells And Unilamellar Vesicles By Incorporation Of Sphingomyelin", J. Biol. Chem., vol. 259: 10823–10826 (1984).*
Lawler, J. F., et al., "Tumor Necrosis Factor–2 Stimulates The Maturation Of Sterol Regulatory Element Binding Protein–1 In Human Hepatocytes Through The Action Of Neutral Sphingomyelinase", J. Biol. Chem., vol. 273: 5053–5059 (1998).*
Shimomura, I., et al., "Nuclear Sterol Regulatory Element–Binding Proteins Activate Genes Responsible For The Entire Program Of Unsaturated Fatty Acid Biosynthesis In Transgenic Mouse Liver", J. Biol. Chem., vol. 273: 35299–35306 (1998).*
Hamanaka, R., et al., "Induction Of Low Density Lipoprotein Receptor And A Transcription Factor SP–1 By Tumor Necrosis Factor In Human Microvascular Endothelial Cells", J. Biol. Chem., vol. 267: 13160–13165 (1992).*
Dawson, P.A., et al., "Sterol–dependent Repression Of Low Density Lipoprotein Receptor Promoter Mediated By 16–Base Pair Sequence Adjacent To Binding Site For Transcription Factor Sp1", J. Biol. Chem., vol. 263: 3372–3379 (1988).
Kim, M.Y., et al., "Identification Of Sphingomyelin Turnover As An Effector Mechanism For The Action Of Tumor Necrosis Factor 2 And γ–Interferon", J. Biol. Chem., vol. 266: 484–489 (1991).
Okazaki, T., et al., "Sphingomyelin Turnover Induced By Vitamin $D_2$ In HL–60 Cells", J. Biol. Chem., vol. 264: 19076–19080 (1989).
Chatterjee, S., et al., "Neutral Sphingomyelinase From Human Urine". J. Biol. Chem., vol. 264: 12554–12561 (1989).
Dobrowsky, R.T., et al., "Activation Of The Sphingomyelin Cycle Through The Low–Affinity Neurotrophin Receptor", Science, vol. 265: 1596–1599 (1994).

(List continued on next page.)

*Primary Examiner*—Theodore J. Criares
*Assistant Examiner*—Jennifer Kim
(74) *Attorney, Agent, or Firm*—Peter F. Corless; Jennifer Rosenfield; Edwards & Angell, LLP

(57) ABSTRACT

Compositions and methods are provided for modulating serum cholesterol in a subject mammal. In one aspect, the invention features novel anti-lipemic drugs that include at least one identified effector of the Low Density Lipoprotein (LDL) receptor and at least one identified serum cholesterol inhibitor. In a particular aspect, the drugs include one identified sphingolipid or protein modifying same linked to one identified serum cholesterol inhibitor. Additionally provided are methods for identifying anti-lipemic drugs capable of modulating the LDL receptor and specifically SREBP-1 maturation, including assays designed to identify pharmacological drugs capable of stabilizing or reducing serum cholesterol levels in a mammal and particularly a human patient.

12 Claims, 16 Drawing Sheets

OTHER PUBLICATIONS

Mathias, S., et al., "Activation Of The Sphingomyelin Signaling Pathway In Intact EL4 Cells And In A Cell–Free System By IL–1β", Science, vol. 259: 519–522 (1993).

Baringa, M., , "Forging A Path To Cell Death", Science, vol. 273: 735–737 (1996).

Brown, M.S., et al., "A Receptor–Mediated Pathway For Cholesterol Homeostasis", Science, vol. 232: 34–47 (1986).

Abe, A., et al., "Improved Inhibitors Of Glucosylceramide Synthase", J. Biochem., vol. 111: 191–196 (1992).

Abe, A., et al. "Structural And Stereochemical Studies Of Potent Inhibitors Of Glucosylceramide Synthase And Tumor Cell Growth", J. Lipid Res., vol. 36: 611–621 (1995).

Inokuchi, J., et al. "Preparation Of The Active Isomer Of 1–phenyl–2–decanoylamino–3–morpholino–1–propanol, Inhibitor Of Murine Glucocerebroside Synthetase", J. Lipid Res., vol. 28: 565–571 (1987).

Bazzoni, F., et al. , "The Tumor Necrosis Factor Ligand And Receptor Families", NEJM, vol. 334: 1717–1725 (1996).

Alessenko, A., et al., "Neutral Sphingomyelinase: Localization In Rat Liver Nuclei And Involvement In Regeneration/Proliferation", Mol. Cell. Biochem., vol. 143: 169–174 (1995).

Tepper, C.G., et al., "Role For Ceramide As An Endogenous Mediator Of Fas–induced Cytotoxicity", Proc. Natl. Acad. Sci. U.S.A., vol. 92, 8443–8447 (1995).

Goldstein, J.L., et al., "Regulation Of The Mevalonate Pathway", Nature, vol. 343, 425–430 (1990).

Cuvillier, O., et al., "Suppression Of Ceramide–mediated Programmed Cell Death By Sphingosine–1–phosphate", Nature, vol. 381, 800–803 (1996).

Mizushima, N., et al., "Ceramide Induces Apoptosis Via CPP32 Activation", FEBS Lett., vol. 395, 267–271 (1996).

X. Wang, et al., "Cleavage Of Sterol Regulatory Element Binding Proteins (SREBPs) by CPP32 During Apoptosis", EMBO, vol. 15, 1012–1020 (1996).

Chan, G., et al., "Sphingomyelin–ceramide Turnover In CD28 Costimulatory Signaling", Eur. J. Immunol., vol. 25: 1999–2004 (1995).

Shukla, A., et al., "Metabolism of D–[$^3$H] threo–1–Phenyl–2–Decanoylamino–3–Morpholino–1–Propanol, An Inhibitor Of Glucosylceramide Synthesis, And The Synergistic Action Of An Inhibitor Of Microsomal Monooxygenase", Journal Of Lipid Research, vol. 32, 713–722 (1991).

Frishman, W.H., et al., "Lovastatin: An HMG–CoA Reductase Inhibitor For Lowering Cholesterol", Medical Clinics Of North America, vol. 73, 437–448 (1989).

Duane, W.C., et al., "Simvastatin, A Competitive Inhibitor Of HMG–CoA Reductase, Lowers Cholesterol Saturation Index Of Gallbladder Bile", Hepatology, vol. 8, 1147–1150 (1988).

Mitchell, J.C., et al., "Effects Of Lovastatin On Biliary Lipld Secretion And Bile Acid Metabolism In Humans", Journal Of Lipid Research, vol. 32, 71–78 (1991).

Copy of Int'l Search Report dated Jun. 15, 2000 re corresponding Int'l. Appln. No. PCT/US00/04657 (five pages).

S. Chatterjee, "Neutral Sphingomyelinase", Advances In Lipid Research, vol. 26:25–48 (1993).

Vunnam, R.R. et al., "Analogs Of Ceramide That Inhibit Glucocerebroside Synthetase In Mouse Brain", Chemistry And Physics Of Lipids, vol. 26: 265–278 (1980).

Carson, K.G. et al., "Studies on Morpholinospingolipids: Potent Inhibitors Of Glucosylceramide Synthase", Tetrahedron Letters, vol. 35: 2659–2662 (1994).

S. Chatterjee, et al., "Purification Of Neutral Sphingomyelinase From Human Urine", Methods In Enzymology, vol. 197: 540–547 (1991).

"The Pharmacological Basis of Therapeutics" 9th ed., 1996, McGraw–Hill pub. p. 884–886.

Chatterjee, "Neutral Sphingomyelinase", Advances in Lipid Research, vol. 26:25–48 (1993).

J. Lawler Jr., et al., *Journal of Biological Chemistry*, 273(9):5053–5059 (1998).

S. Chatterjee, *Chemistry and Physics of Lipids*, 102(1–2):79–96 (1999).

* cited by examiner

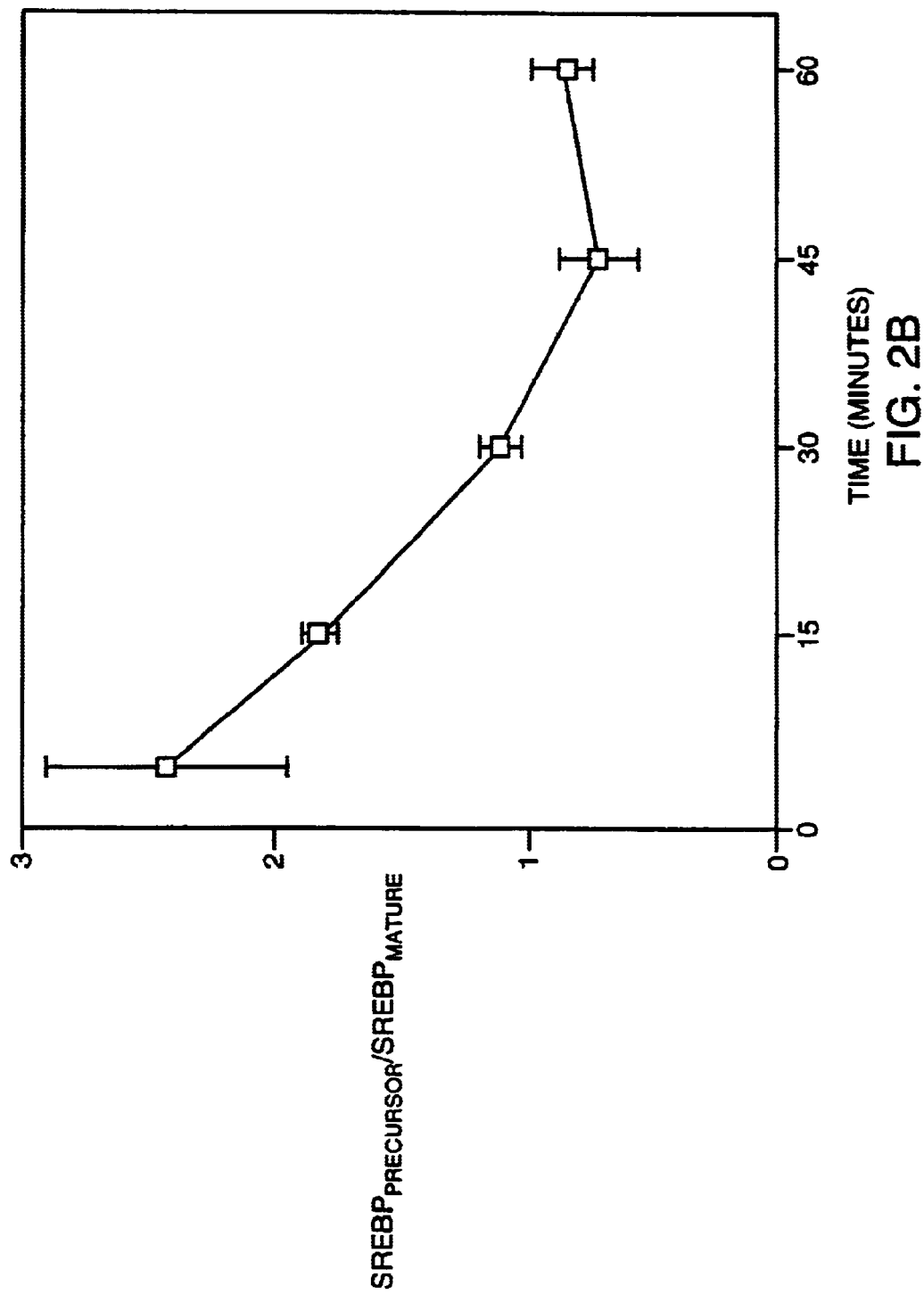

TNF-α

SPHINGOMYELINASE $C_2$-CERAMIDE

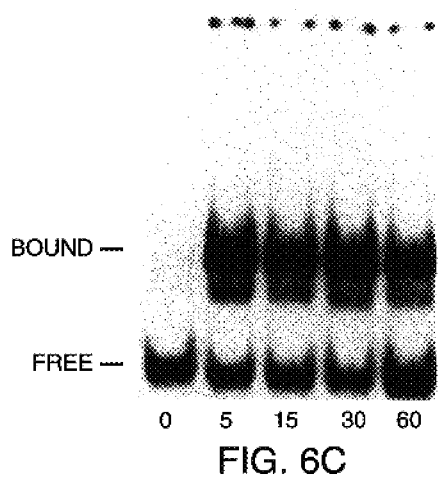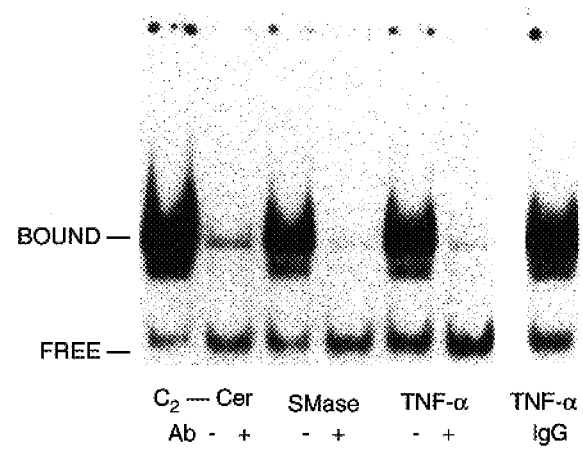
FIG. 6C
FIG. 6D

LDL-r—
mRNA 1    2    3

P—

M—

1    2    3    4    5

| | | | | | |
|---|---|---|---|---|---|
| ATGATGACAT | ATCACGAAAC | GCGCGCGGTTG | GCTCAAAGCG | ACTTACAGCA | ACTCTATGCG | 60
| GCACTTGAAA | CAACTGAATT | TGGCGCTTAC | TTTGCGACAC | CCGCTGATGA | TACTTTACGT | 120
| TTTGGCATTG | GCGCAATCGC | TACGGCAAAA | ACGGCTCAGG | CATTACAAGG | TGCGGTTGTT | 180
| TTTGGTGCGC | AGTCATTTGA | TGAACAAGAG | TACCCGCAGT | CTGAATTGAT | GGCGGGTTTT | 240
| TGGTTTGTCC | CCGAAGTGAT | GGTGACCATC | GCGGCAGATA | AAATCACGTT | CGGATCAGAT | 300
| ACCGTATCTG | ATTTTACGAC | GTGGCTGGCG | CAGTTCGTGC | CAAAACAGCC | AAATACGGTG | 360
| ACCACTAGTC | ATGTGACAGA | TGAAGTGGAT | TGGATCGAAC | GGACAGAGAA | TTTGATTGAT | 420
| ACCTTAGCCA | TCGATCAAAA | CTTAGCCAAA | GTCGTTTTTG | GTCGGCAACA | GACCCTGCAG | 480
| TTATCCGACA | CGTTACGACT | GGCACAAATT | ATTCGTGCGT | TAGCTGAGCA | GGCGAATACG | 540
| TATCATGTGG | TTTTAAAGCG | ACATGATGAA | TTGTTTATTT | CAGCAACACC | GGAACGGTTA | 600
| GTGGCTATGT | CAGGTGGTCA | GATCGCTACG | GCGGCGGTCG | CTGGGACAAG | CCGGCGCGGG | 660
| ACGGATGGCG | CTGACGATAT | CGCGTTAGGC | GAAGCGTTGT | TAGCCAGTCA | GAAAAACCGC | 720
| ATTGAACATC | AATATGTCGT | GGCAAGTATC | ACGACACGCT | TGCAAGACGT | GACGACGTCG | 780
| CTAAAGGTGC | CGGCCATGCC | AAGTTTACTC | AAAAATAAGC | AAGTTCAGCA | TTTGTACACA | 840
| CCAATTACAG | GGGACATTGC | GGCACATTTA | AGTGTGACCG | CGATTGTTGA | CCGCTTGCAT | 900
| CCAACACCAG | CACTGGGGTGG | CGTCCCACGT | GAAGCGGCCC | TGTATTACAT | TGCGACCCAT | 960
| GAGAAGACAC | CTCGTGGCTT | GTTTGCAGGT | CCTATTGGCT | ATTTTACCGC | AGATAATAGT | 1020
| GGGGAATTTG | TGGTTGGCAT | CCGTTCCATG | TATGTGAATC | AAACGCAGCG | ACGAGCAACT | 1080
| TTATTTGCTG | GTGCCGGGAT | TGTGGCTGAC | TCCGATGCGC | AACAAGAATA | TGAAGAAACT | 1140
| GGGTTGAAAT | TTGAACCCAT | GCGGCAATTG | TTAAAGGACT | ACAATCATGT | CGAATGA | 1197

FIG. 11

```
Met Met Thr Tyr His Glu Thr Arg Ala Leu Ala Gln Ser Asp Leu Gln
 1           5                     10                  15
Gln Leu Tyr Ala Ala Leu Glu Thr Thr Glu Phe Gly Ala Tyr Phe Ala
                 20                  25                  30
Thr Pro Ala Asp Asp Thr Leu Arg Phe Gly Ile Gly Ala Ile Ala Thr
             35                  40                  45
Ala Lys Thr Ala Gln Ala Leu Gln Gly Ala Val Phe Gly Ala Gln Ser
         50                  55                  60
Phe Asp Glu Gln Glu Tyr Pro Gln Ser Glu Leu Met Ala Gly Phe Trp
 65                  70                  75                  80
Phe Val Pro Glu Val Met Val Thr Ile Ala Ala Asp Lys Ile Thr Phe
                 85                  90                  95
Gly Ser Asp Thr Val Ser Asp Phe Thr Thr Trp Leu Ala Gln Phe Val
             100                 105                 110
Pro Lys Gln Pro Asn Thr Val Thr Thr Ser His Val Thr Asp Glu Val
         115                 120                 125
Asp Trp Ile Glu Arg Thr Glu Asn Leu Ile Asp Thr Leu Ala Ile Asp
     130                 135                 140
Gln Thr Leu Ala Lys Val Val Phe Gly Arg Gln Gln Thr Leu Gln Leu
145                 150                 155                 160
Ser Asp Thr Leu Arg Leu Ala Gln Ile Ile Arg Ala Leu Ala Glu Gln
             165                 170                 175
Ala Asn Thr Tyr His Val Val Leu Lys Arg His Asp Glu Leu Phe Ile
             180                 185                 190
Ser Ala Thr Pro Glu Arg Leu Val Ala Met Ser Gly Gly Gln Ile Ala
         195                 200                 205
Thr Ala Ala Val Ala Gly Thr Ser Arg Arg Gly Thr Asp Gly Ala Asp
     210                 215                 220
Asp Ile Ala Leu Gly Glu Ala Leu Leu Ala Ser Gln Lys Asn Arg Ile
225                 230                 235                 240
Glu His Gln Tyr Val Val Ala Ser Ile Thr Thr Arg Leu Gln Asp Val
                 245                 250                 255
Thr Thr Ser Leu Lys Val Pro Ala Met Pro Ser Leu Leu Lys Asn Lys
             260                 265                 270
Gln Val Gln His Leu Tyr Thr Pro Ile Thr Gly Asp Ile Ala Ala His
         275                 280                 285
Leu Ser Val Thr Ala Ile Val Asp Arg Leu His Pro Thr Pro Ala Leu
     290                 295                 300
Gly Gly Val Pro Arg Glu Ala Ala Leu Tyr Tyr Ile Ala Thr His Glu
305                 310                 315                 320
Lys Thr Pro Arg Gly Leu Phe Ala Gly Pro Ile Gly Tyr Phe Thr Ala
             325                 330                 335
Asp Asn Ser Gly Glu Phe Val Val Gly Ile Arg Ser Met Tyr Val Asn
         340                 345                 350
Gln Thr Gln Arg Arg Ala Thr Leu Phe Ala Gly Ala Gly Ile Val Ala
     355                 360                 365
Asp Ser Asp Ala Gln Gln Glu Tyr Glu Thr Gly Leu Lys Phe Glu
370                 375                 380
Pro Met Arg Gln Leu Leu Lys Asp Tyr Asn His Val Glu
385                 390                 395
```

FIG. 12

| COMPOUND | TARGET | RESULT |
|---|---|---|
| CERAMIDE (C-2, C-6, C-8, NATURAL) HEXOSE - G-P | LIVER | INCREASE LDL RECEPTORS (DECREASE PLASMA CHOLESTEROL) |
| CERAMIDE ~ HEXOSE - G-P | LIVER | INCREASE LDL RECEPTORS (DECREASE HMG-GA REDUCTASE) |
| N-SMase ~ LIPOSOME (TOPICAL USE ONLY) | SKIN | DECREASE PLANAR XANTHOMA (E.G., EYELIDS) |
| PHH1~HEXOSE – 6 – P ± STATINS | LIVER | INCREASE LDL RECEPTORS (DECREASE PLASMA CHOLESTEROL) |
| PHH-II~HEXOSE – 6 – P ± STATINS | LIVER | IBID. |
| PHH-1~D – PDMP | KIDNEY | KILL TUMORS (APOPTOSIS) AND REDUCE CHOLESTEROL SUPPLY |
| PHH-1~D – PDMP | KIDNEY | KILL AND/OR PRESENT TUMORS AND REDUCE CHOLESTEROL SUPPLY |

~ = CHEMICAL BOND

FIG. 13

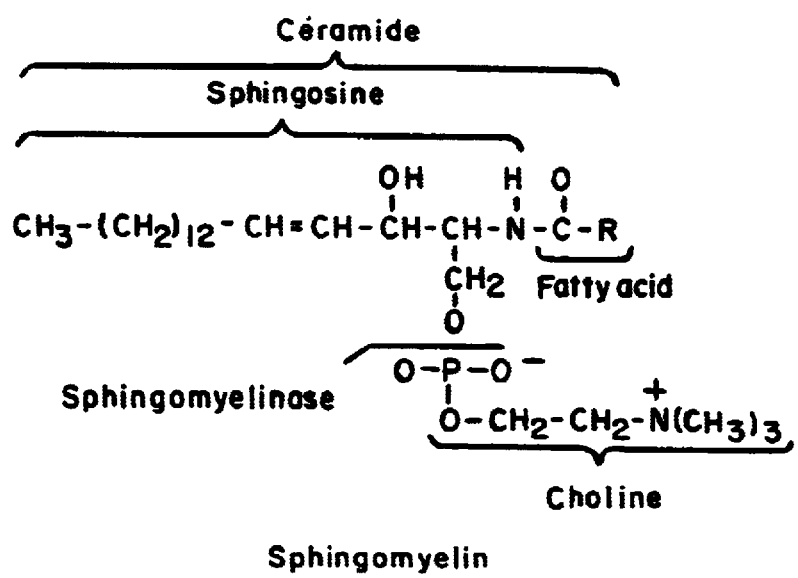
FIG. 15A
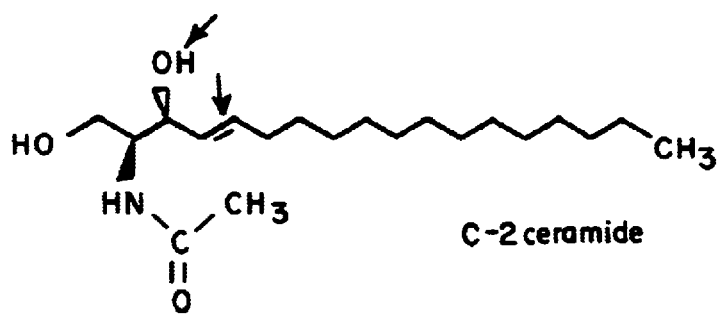
C-2 ceramide
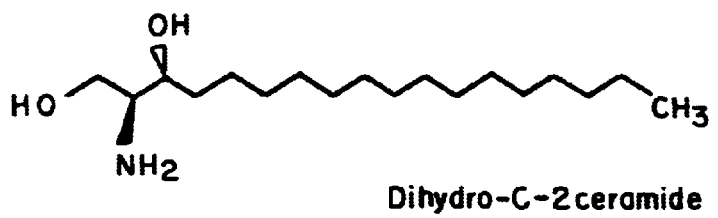
Dihydro-C-2 ceramide
FIG. 15B

SEQUENCE LISTING

<160> NUMBER OF SEQ ID NOS: 2

<210> SEQ ID NO 1
<211> LENGTH: 1197
<212> TYPE: DNA
<213> ORGANISM: Human
<220> FEATURE:
<221> NAME/KEY: gene
<222> LOCATION: (1)...(1197)
<223> OTHER INFORMATION: cDNA

<400> SEQUENCE: 1

```
atgatgacat atcacgaaac gcgcgcgttg gctcaaagcg acttacagca actctatgcg      60
gcacttgaaa caactgaatt tggcgcttac tttgcgacac ccgctgatga tactttacgt     120
tttggcattg gcgcaatcgc tacggcaaaa acggctcagg cattacaagg tgcggttgtt     180
tttggtgcgc agtcatttga tgaacaagag tacccgcagt ctgaattgat ggcgggtttt     240
tggtttgtcc ccgaagtgat ggtgaccatc gcggcagata aaatcacgtt cggatcagat     300
```

-continued

```
accgtatctg attttacgac gtggctggcg cagttcgtgc aaaacagcc aaatacggtg      360
accactagtc atgtgacaga tgaagtggat tggatcgaac ggacagagaa tttgattgat      420
accttagcca tcgatcaaac cttagccaaa gtcgttttg gtcggcaaca gaccctgcag      480
ttatccgaca cgttacgact ggcacaaatt attcgtgcgt tagctgagca ggcgaatacg      540
tatcatgtgg ttttaaagcg acatgatgaa ttgtttattt cagcaacacc ggaacggtta      600
gtggctatgt caggtggtca gatcgctacg gcggcggtcg ctgggacaag ccggcgcggg      660
acggatggcg ctgacgatat cgcgttaggc gaagcgttgt tagccagtca gaaaaaccgc      720
attgaacatc aatatgtcgt ggcaagtatc acgacacgct gcaagacgt gacgacgtcg      780
ctaaaggtgc cggccatgcc aagtttactc aaaaataagc aagttcagca tttgtacaca      840
ccaattacag gggacattgc ggcacattta agtgtgaccg cgattgttga ccgcttgcat      900
ccaacaccag cactgggtgg cgtcccacgt gaagcggccc tgtattacat tgcgacccat      960
gagaagacac ctcgtggctt gtttgcaggt cctattggct attttaccgc agataatagt     1020
ggggaatttg tggttggcat ccgttccatg tatgtgaatc aaacgcagcg acgagcaact     1080
ttatttgctg gtgccgggat tgtggctgac tccgatgcgc aacaagaata tgaagaaact     1140
gggttgaaat ttgaacccat gcggcaattg ttaaaggact acaatcatgt cgaatga       1197
```

<210> SEQ ID NO 2
<211> LENGTH: 397
<212> TYPE: PRT
<213> ORGANISM: Human

<400> SEQUENCE: 2

```
Met Met Thr Tyr His Glu Thr Arg Ala Leu Ala Gln Ser Asp Leu Gln
 1               5                  10                  15

Gln Leu Tyr Ala Ala Leu Glu Thr Thr Glu Phe Gly Ala Tyr Phe Ala
            20                  25                  30

Thr Pro Ala Asp Asp Thr Leu Arg Phe Gly Ile Gly Ala Ile Ala Thr
        35                  40                  45

Ala Lys Thr Ala Gln Ala Leu Gln Gly Ala Val Phe Gly Ala Gln Ser
    50                  55                  60

Phe Asp Glu Gln Glu Tyr Pro Gln Ser Glu Leu Met Ala Gly Phe Trp
65                  70                  75                  80

Phe Val Pro Glu Val Met Val Thr Ile Ala Ala Asp Lys Ile Thr Phe
                85                  90                  95

Gly Ser Asp Thr Val Ser Asp Phe Thr Thr Trp Leu Ala Gln Phe Val
            100                 105                 110

Pro Lys Gln Pro Asn Thr Val Thr Thr Ser His Val Thr Asp Glu Val
        115                 120                 125

Asp Trp Ile Glu Arg Thr Glu Asn Leu Ile Asp Thr Leu Ala Ile Asp
    130                 135                 140

Gln Thr Leu Ala Lys Val Val Phe Gly Arg Gln Gln Thr Leu Gln Leu
145                 150                 155                 160

Ser Asp Thr Leu Arg Leu Ala Gln Ile Ile Arg Ala Leu Ala Glu Gln
                165                 170                 175

Ala Asn Thr Tyr His Val Val Leu Lys Arg His Asp Glu Leu Phe Ile
            180                 185                 190

Ser Ala Thr Pro Glu Arg Leu Val Ala Met Ser Gly Gly Gln Ile Ala
        195                 200                 205

Thr Ala Ala Val Ala Gly Thr Ser Arg Arg Gly Thr Asp Gly Ala Asp
    210                 215                 220
```

```
Asp Ile Ala Leu Gly Glu Ala Leu Leu Ala Ser Gln Lys Asn Arg Ile
225                 230                 235                 240

Glu His Gln Tyr Val Val Ala Ser Ile Thr Thr Arg Leu Gln Asp Val
                245                 250                 255

Thr Thr Ser Leu Lys Val Pro Ala Met Pro Ser Leu Leu Lys Asn Lys
            260                 265                 270

Gln Val Gln His Leu Tyr Thr Pro Ile Thr Gly Asp Ile Ala Ala His
        275                 280                 285

Leu Ser Val Thr Ala Ile Val Asp Arg Leu His Pro Thr Pro Ala Leu
    290                 295                 300

Gly Gly Val Pro Arg Glu Ala Ala Leu Tyr Tyr Ile Ala Thr His Glu
305                 310                 315                 320

Lys Thr Pro Arg Gly Leu Phe Ala Gly Pro Ile Gly Tyr Phe Thr Ala
                325                 330                 335

Asp Asn Ser Gly Glu Phe Val Val Gly Ile Arg Ser Met Tyr Val Asn
            340                 345                 350

Gln Thr Gln Arg Arg Ala Thr Leu Phe Ala Gly Ala Gly Ile Val Ala
        355                 360                 365

Asp Ser Asp Ala Gln Gln Glu Tyr Glu Glu Thr Gly Leu Lys Phe Glu
    370                 375                 380

Pro Met Arg Gln Leu Leu Lys Asp Tyr Asn His Val Glu
385                 390                 395
```

COMPOSITIONS AND METHODS FOR MODULATING SERUM CHOLESTEROL

This application claims the benefit of U.S. provisional application No. 60/121,447, filed Feb. 24, 1999, which is incorporated herein by reference in its entirety.

STATEMENT OF GOVERNMENT INTEREST

Funding for the present invention was provided in part by the Government of the United States by virtue of National Institute of Health Grants R0-1 DK-31722 and P50-HL4812. Thus, the Government of the United States has certain rights in and to the invention claimed herein.

FIELD OF THE INVENTION

The present invention relates to compositions and methods for modulating serum cholesterol. In one aspect, the invention features novel anti-lipemic drugs that include at least one identified effector of the Low Density Lipoprotein (LDL) receptor and at least one identified serum cholesterol inhibitor. In a particular aspect, the anti-lipemic drug includes at a sphingolipid or protein modifying same linked to the serum cholesterol inhibitor. Additionally provided are methods for using the anti-lipemic drugs to significantly stabilize or reduce serum cholesterol levels in a subject mammal and particularly a human patient.

BACKGROUND OF THE INVENTION

There is nearly universal agreement that cholesterol is a key lipid constituent of cell membranes. Cholesterol is generally understood to be essential for normal growth and viability of most higher organisms. Too much serum cholesterol has been correlated with life threatening lipid related diseases including hyperlipoproteinemia, stoke, coronary heart disease, and especially atherosclerosis and related conditions. See generally Stryer, L. (1988) in *Biochemistry*, $3^{rd}$ Ed. W. H. Freeman and Co. New York, pp. 547–574; and Brown, M. S. and Goldstein, J. L. (1993) in *The Pharmacological Basis of Therapeutics* ($8^{th}$ Ed.) Gilman, A. G. et al. eds. McGraw-Hill/New York, pp. 874–896.

The regulation of serum cholesterol in mammals and particularly primates has attracted significant attention. It is often reported that regulation of cholesterol homeostasis in humans and other mammals involves regulation of cholesterol production, bile acid biosynthesis and catabolism of specific serum cholesterol carriers. Important serum cholesterol carriers are called LDL (low density lipoprotein) particles. The LDL receptor has been reported to facilitate internalization of the LDL particle into those cells in need of cholesterol. See e.g., Brown, M. S. and Goldstein, J. L. (1986) *Science* 232: 34–47; and Goldstein, J. L. and Brown, (1986) *Nature*, 348: 425; and references cited therein.

The LDL receptor has been disclosed as impacting serum cholesterol levels in humans. For example, there has been recognition that cells with enough cholesterol do not make sufficient LDL receptors, thereby reducing or even blocking uptake of cholesterol by the cell. In this instance, serum cholesterol levels rise substantially which can contribute to the development or severity of disease. Conversely, cells in need of cholesterol often have capacity to make more LDL receptors, thereby facilitating a decrease in serum cholesterol. Accordingly, there has been specific attention focused on regulating the LDL receptor as one therapeutic approach for stabilizing or reducing serum cholesterol levels in human patients.

In particular, it has been reported that transcription of the LDL receptor gene is suppressed when sterols accumulate and induced when sterols are depleted. Sterol sensitivity is thought to be conferred by a 10 basepair (bp) sequence upstream of the LDLr gene known as the sterol regulatory element (SRE). It has been disclosed that the mature form of the sterol regulatory element binding protein-1 (SREBP-1) binds to the SRE and promotes transcription.

There have been additional reports that the activity of SREBP-1 is influenced by sterol induced proteolysis. There is recognition that the SREBP-1 proteolysis is impacted in some settings by a cell receptor termed "cytokine tumor necrosis factor" (TNF-α).

In particular, the TNF-α receptor has been reported to influence a wide range of biological effects. However, the TNF-α receptor remains incompletely characterized. Elucidation of TNF-α pathways is sometimes complicated by presence of at least two TNF receptors. The receptors share some common downstream effectors but also signal via receptor specific pathways. See the references cited below for additional disclosure relating to the TNF-α receptor.

There has been understanding that one consequence of TNF signaling is the activation of neutral sphingomyelinase (N-SMase). Neutral sphingomyelinase is a membrane bound enzyme that catalyzes the hydrolysis of sphingomyelin to ceramide and phosphocholine at a pH optima of 7.4. The role of neutral sphingomyelinase in signal transduction has primarily been related to ability to generate the lipid second messenger ceramide. In addition to TNF-α, Fas receptor ligand, vitamin $D_3$, interleukin-1β, nerve growth factor, anti-CD28 antibodies and γ-interferon have all been shown to increase ceramide levels.

In particular, sphingomyelinases type-C (E.C. 3.1.4.12) are a group of phospholipases that catalyze the hydrolytic cleavage of sphingomyelin via the following reaction (1).

$$\text{Sphingomyelin} \rightarrow \text{Ceramide} + \text{Phosphocholine} \tag{1}$$

See S. Chatterjee, *Adv. Lipid Res.*, 26:25–48 (1993); S. Chatterjee et al., *J. Biol. Chem.*, 264:12,534–12,561 (1989); and S. Chatterjee et al., *Methods in Enzymology, Phospholipase*, 197:540–547 (1991).

In addition to the biological roles of sphingomyelin and ceramide in signal transduction pathways involving cell regulation, more recent evidence has emerged suggesting that sphingomyelinases may be involved in cholesterol homeostasis and particularly induction of LDL receptor activity. See S. Chatterjee, *Advances in Lipid Research*, 26:25–48 (1993). Additional work supports a possible role of ceramide in programmed cell death and/or "apoptosis" and activation of the gene for nuclear factor (NF)-kB. See A. Alessenko and S. Chatterjee, *Mol. Cell. Biochem.*, 143:169 (1995).

It has been suggested that certain enzymes involved in making cholesterol exert a significant effect on cholesterol homeostasis. Accordingly, there has been substantial interest in identifying drugs with capacity to modulate these enzymes especially to stabilize or reduce serum cholesterol to tolerable ranges. Illustrative agents include commercially available serum cholesterol inhibitors such as fluvastatin, simvastatin, lovastatin, pravastatin, and atorvastatin. See Brown, M. S. and Goldstein, J. L. (1993), supra for additional disclosure relating to these and other agents such as mevinolin (compactin).

Although some clinical benefit has been reported to follow use of these and other serum lowering agents, there have been reports of significant side-effects. See e.g., Brown, M. S. and Goldstein, J. L. (1993), supra; and *Physicians' Desk Reference* 1997 (515st ed.) Medical Economics Co. Accordingly, there is a need to have drugs that exhibit more desirable characteristics such as enhanced potency and better patient tolerance. There is a specific need to reduce levels of administered cholesterol lowering agents for some patients.

There is also a need to identify drugs that can modulate the SREBP-1 protein and especially the LDL receptor. Moreover, methods for identifying pharmacological drugs of interest by automated, high throughput drug screening have become increasing relied upon in a variety of pharmaceutical and biotechnology drug development programs. Unfortunately, requisite drugs for such high throughput screening assays are not widespread. A significant reason for lack of progress in this area is insufficient understanding of molecules (i.e. effectors) that impact SREBP-1 and the LDL receptor.

It thus would be desirable to have anti-lipemic drugs with dual capacity to modulate the LDL receptor and serum cholesterol levels. It would be particularly desirable if such anti-lipemic drugs could be administered to subject mammal at doses near or below those presently used with many serum cholesterol inhibitors. It would be further desirable to have effective in vitro and in vivo assays for identifying drugs with potential to modulate the LDL receptor particularly involving SREBP-1 protein maturation.

SUMMARY OF THE INVENTION

The present invention generally relates to compositions and methods for modulating serum cholesterol in a subject mammal. In one aspect, the invention features novel anti-lipemic drugs that include at least one identified effector of the Low Density Lipoprotein (LDL) receptor and at least one identified serum cholesterol inhibitor. In a particular aspect, the drugs include one identified sphingolipid or protein modifying same linked to one identified serum cholesterol inhibitor. Additionally provided are methods for identifying anti-lipemic drugs capable of modulating the LDL receptor and specifically SREBP-1 maturation, including assays designed to identify pharmacological drugs capable of stabilizing or reducing serum cholesterol levels in a mammal and particularly a human patient.

We have discovered a wide spectrum of compositions and methods for treating or preventing disorders modulated by cholesterol. Sometimes the disorders will be referred to herein as "cholesterol related disorders" or a similar term. More specifically, we have identified anti-lipemic drugs that include at least one identified effector of the LDL receptor, and particularly an effector of SREBP-1 and at least one identified serum cholesterol inhibitor. Particular anti-lipemic drugs of this invention usually have one of each component although drugs having multiple effectors and inhibitors (e.g., between from about 2 to 5 of each) are contemplated. Preferred anti-lipemic drugs feature specifically defined characteristics such as capacity to stabilize or reduce serum cholesterol levels in a subject mammal as determined by in vitro or in vivo assays described below.

More specifically, the present invention provides a variety of specific anti-lipemic drugs and methods for using same for the treatment or prevention of one or more than one cholesterol related disorder in a subject mammal. Illustrative disorders are known in the field and include hyperlipoproteinemia including hypercholesterolemia, stroke, obesity, compulsive eating disorders, cardiac disease including atherosclerosis, cerebral atherosclerosis, cholesteryl ester storage disorder, liver disease including organ transplantation failure and cirrhosis; diseases of the biliary system, and viral infection, particularly those infections facilitating encephalitis or related disorders.

Particular anti-lipemic drugs in accord with this invention include one SREBP-1 effector and one synthetic or semi-synthetic inhibitor of an enzyme associated with cholesterol biosynthesis. Preferred enzymes have been extensively characterized and include 3-hydroxy-3-methylglutaryl (HMG) CoA reductase and HMG CoA synthetase. Additionally contemplated anti-lipemic drugs feature, as the effector component, an identified caspase, particularly the cpp32 protease (caspase-3), neutral sphingomyelinase (N-SMase), ceramide, SREBP-1 (precursor), or SREBP-1 (mature). Effective fragments of the N-SMase, cpp32 protease, SREBP-1 (precursor), or the SREBP-1 (mature) protein are contemplated as effector molecules within the scope of this invention.

Additionally specific anti-lipemic drugs include one effector of SREBP-1 which effector can be a sphingolipid, e.g., sphingomyelin or ceramide; or N-SMase or an effective fragment thereof. In embodiments in which the anti-lipemic drug includes ceramide, that ceramide molecule is preferably naturally-occurring (i.e., can be isolated in substantially pure formn from a biological source). A more preferred ceramide for use in the drug is any one of C-2, C-4, C-6 or C-8 ceramide. A preferred N-SMase molecule is encoded by specific nucleotide sequences disclosed herein including those encoding enzymatically active forms of that enzyme and effective fragments thereof. Preferred effectors in accord with this invention demonstrate substantial capacity to modulate the LDL receptor and especially maturation of the SREBP-1 protein as determined by specific assays described below.

As discussed, particular anti-lipemic drugs of this invention include a suitable SREBP-1 effector such as sphingolipid, particularly a sphingomyelin or ceramide, N-SMase or effective fragment thereof, although other drugs may include other effectors as needed. In this embodiment, the anti-lipemic drug further includes the inhibitor of HMG CoA reductase. It is generally preferred that the effector and the inhibitor are be combined in a way to facilitate function for which the drug was intended. A preferred function is to stabilize or reduce serum cholesterol as determined by a conventional in vivo assays defined below. In most instances, covalent attachment between the effector and the inhibitor will be preferred although other associations will be suitable for some applications. Preferred cholesterol inhibitors have recognized capacity to inhibit the reductase, thereby lowering serum cholesterol. Illustrative inhibitors include commercially available serum cholesterol inhibitors acceptable for human use, e.g., fluvastatin, simvastatin, lovastatin, pravastatin, mevinolin (compactin), atorvastatin; or a clinically acceptable derivative thereof.

In a particular embodiment, the anti-lipemic drugs include one effector of the SREBP-1 protein, e.g., the N-SMase or effective fragment; or a sphingolipid. In this example, the effector is also preferably associated with the inhibitor of HMG CoA reductase. By the term "associated" or related term is meant that the SREBP-1 effector and the inhibitor are attached by at least one bond preferably at least on covalent bond. Particular examples of bonding are described below. In some instances, the association can also be provided by a suitable combination of covalent and non-covalent chemical bonds. Alternatively, association between the SREBP-1 effector and the inhibitor can be provided by essential co-administration of the effector and the inhibitor to a desired subject mammal. More specific methods for making and using the drugs of this invention are provided in the discussion and examples which follow.

In one embodiment, the anti-lipemic drug includes the sphingolipid attached to the inhibitor by at least one covalent bond. As noted, preferred are recognized cholesterol inhibitors such as fluvastatin, simvastatin, lovastatin, pravastatin, mevinolin (compactin), atorvastatin. In this illustration, the sphingolipid is preferably ceramide or a related molecule, particularly any one of the preferred ceramides described previously, which ceramide is covalently linked to a reactive hydroxyl group on the inhibitor molecule. Also in this example, the hydroxyl group of the inhibitor is usually covalently linked to a reactive carbon atom on the ceramide such as the C-3 carbon.

Additional anti-lipemic drugs of this invention include at least one bifunctional spacer group, typically a heterobifunctional spacer group, which group spaces the SREBP-1 effector from the inhibitor or other drug moiety. A particular example of this type of anti-lipemic drug includes one SREBP-1 effector covalently linked to one heterobifunctional spacer group. That spacer group is preferably covalently linked to the serum cholesterol inhibitor. Typically, the bifunctional spacer is linked to suitably reactive chemical group on the effector and the inhibitor, usually specifically reactive carbon atoms and hydroxyl groups, respectively.

Further anti-lipemic drugs in accord with the present invention include one effector of SREBP-1 such as the neutral sphingomyelinase (N-SMase) or an effective fragment thereof. A preferred drug includes the N-SMase or the fragment in association with an inhibitor of HMG CoA reductase or HMG CoA synthetase as described previously. Preferred examples of the N-SMase and fragment are provided in the examples and discussion which follow.

Further contemplated anti-lipemic drugs include the effector of SREBP-1, preferably the neutral sphingomyelinase (N-SMase) or the fragment thereof; which effector is covalently linked to one inhibitor of the HMG CoA reductase. Preferred inhibitors of the reductase have already been discussed. Preferably, the covalent linkage is made by binding a chemically reactive group on the enzyme or fragment, preferably an amide bond. More particular anti-lipemic drugs are disclosed below featuring an amide linkage between the enzyme or fragment and the serum cholesterol inhibitor.

Preferred anti-lipemic drugs of this invention are generally formulated to suit intended use and specifically include those drugs formatted for topical or related use. Additionally, the invention includes anti-lipemic drugs that include components sufficient to provide the drug as a liposome formulation suitable for in vitro or in vivo use. Methods for making and using such preferred drugs are described below.

In general, therapeutic methods in accord with this invention include administering to a subject, particularly a mammal such as a primate, especially a human, a therapeutically effective amount of at least one anti-lipemic drug of interest. That drug can be administered as a sole active agent. Alternatively, the anti-lipemic drug can be administered in combination with other drugs or agents exhibiting a desired pharmacological activity. In most cases, the amount of anti-lipemic drug use will be one which exhibits good activity in a standard in vitro or in vivo assay described below.

As discussed, the anti-lipemic drugs of this invention advantageously provide dual "anti-cholesterol" activity, ie, by increasing LDL receptor activity, particularly by enhancing LDL receptor levels; and by reducing serum cholesterol levels. Particular in vitro and in vivo assays to detect and quantitate these activities are provided below and in the discussion and examples which follow.

As an illustration, preferred anti-lipemic drugs of this invention are capable of stimulating production of the mature form of SREBP-1 (maturation) by at least about 2 fold, as determined by a standard SREBP-1 proteolysis (maturation) assay. That assay is provided below and generally involves monitoring in a time and dose dependent manner, the maturation of the SREBP-1 protein. Mature SREBP-1 protein is believed to move to the nucleus and stimulate production of LDL receptor.

Additionally preferred anti-lipemic drugs of this invention are capable of increasing LDL receptor mRNA levels by at least about 10%, 20%, 30%, 40%, 50%, 60%, 70%, 80, or 90% as determined by Northern blot or related mRNA detection assay. An exemplary Northern blot assay for detecting and optionally quantitating LDL receptor mRNA levels are provided below.

Also preferred anti-lipemic drugs of this invention exhibit an $ID_{50}$ of between from about 20%, 30%, 40%, 50%, 60%, or 70% to about 90% as determined in a standard HMG CoA reductase assay. In this assay, the activity of the reductase enzyme is monitored in the presence and absence (control) of the anti-lipemic agent. An example of the standard HMG CoA reductase assay is provided below.

Further preferred anti-lipemic drugs are capable of significantly reducing serum cholesterol as determined by a standard serum cholesterol assay. Preferably, an administered anti-lipemic drug is capable of reducing serum cholesterol in a subject mammal by at least about 5%, 10% to 20% or 30%, 40%, 50%, 60% or 70%. An example of the assay is described below. Typically, the reduction in serum cholesterol is monitored with respect to a suitable control subject. The serum cholesterol assays are optimally performed in vivo and preferably include use of a recognized animal model such as specific rabbit and mouse strains provided below.

Preferred animal models for use in the serum cholesterol assay or other suitable assay disclosed herein are generally recognized test systems for an identified cholesterol related disease. Typically such animal models include commercially available in-bred strains of rabbits or mice, e.g., the Watanabe heritable hyperlipidemic rabbit and the apolipoprotein E negative mouse. In this example, the reduction in serum cholesterol can be evaluated using well-known testing strategies adopted for use with the specific animal model. However for some applications it may be useful to test a desired anti-lipemic drug on a normal ("wild-type") animal such as those genetically defined (e.g., isogenic) wild-type animal strains known in the field.

The anti-lipemic drugs of this invention are preferably tested by at least one and preferably all of the standard assays summarized above. Preferred are anti-lipemic drugs that demonstrate about the stated activity ranges in one or more of the assays.

Significantly, use of multiple testing strategies (e.g., a combination of one in vitro and/or in vivo assays) with a single anti-lipemic drug can extend the selectivity and effectiveness of the testing as needed. That is, the testing strategy can be tailored for treatment or prevention of a particular cholesterol related disease or group of patients if required.

Such broad spectrum testing provides additional advantages. For example, preferred anti-lipemic drugs have capacity to enhance LDL receptor activity (typically by enhancing production of the LDL receptor) and provide for a reduction in serum cholesterol level. Thus by providing such dual "anti-cholesterol" activity, the invention is a significant advance over prior therapies and agents that have been reported to reduce serum cholesterol in one way, usually by targeting cholesterol biosynthesis. Accordingly, preferred anti-lipemic drugs of this invention feature better activity, can be administered at lower dosages then prior agents. Patient tolerance of the anti-lipemic drugs will also be positively impacted.

In another aspect, the invention includes methods for modulating and particularly reducing serum cholesterol level in a mammal. In this embodiment, the methods generally include administering to the mammal a therapeutically effective amount of at least one and typically one of the anti-lipemic drugs disclosed herein.

Also provided are methods for modulating LDL receptor levels in a mammal in which the method includes administering to the mammal a therapeutically effective amount of at least one and typically one of the anti-lipemic drugs disclosed herein.

The present invention also provides methods treating a disorder in a mammal having or suspected of having high serum cholesterol levels. In this embodiment, the method includes administering to the mammal a therapeutically effective amount of at least one of the anti-lipemic drugs disclosed herein. A preferred mammal is a primate and especially a human patient, e.g., those susceptible to coronary heart disease, obesity, eating disorders or other cholesterol related disorders described herein. Accordingly, the methods are especially applicable to a subject mammal such as a human patient who has been diagnosed as having, is suspected of having, or is susceptible to a high serum cholesterol level, e.g., through adverse genetic or dietary influences.

Also provided by this invention are methods for modulating serum cholesterol level in a mammal in which the method includes administering to the mammal a therapeutically effective amount of at least one of the anti-lipemic drugs disclosed herein. In this embodiment, the SREBP-1 effector is preferably neutral shpingomyelinase (N-SMase) or an effective fragment thereof; or a sphingolipid such as cermide. Preferred methods employ a primate such as a human patient. Preferred anti-lipemic agents for use in the methods are typically tested for activity using a recognized animal model for a cholesterol related disorder and especially atherosclerosis, e.g., the Watanabe heritable hyperlipidemic rabbit or an apolipoprotein E negative mouse discussed previously.

Additionally contemplated are methods for modulating LDL receptor in a mammal in which the methods include administering to the mammal a therapeutically effective amount of at least one of the anti-lipemic drugs disclosed herein. The modulation is preferably an increase in the synthesis (or sometimes decrease in the degradation of) the LDL receptor. In this example, the SREBP-1 effector is neutral sphingomyelinase (N-SMase) or an effective fragment thereof; or a sphingolipid such as ceramide. Methods for evaluating an increase or decrease in LDL receptor levels are known in the field and involve, e.g., molecular and immunological approaches using anti-LDL antibodies capable of detecting and quantitating LDL receptor in vitro or in vivo.

Particular methods of this invention involve use of at least one suitable anti-lipemic drug which includes one effector of SREBP-1 associated with an identified inhibitor of serum cholesterol as discussed herein. In this example, that effector is preferably a sphingolipid such as ceramide. Preferred examples of ceramide include naturally occurring ceramide and other ceramide forms as discussed previously. As discussed, preferred methods are conducted using a mammalian subject such as a primate and especially a human patient who has been diagnosed as having, is suspected of having, or is susceptible to a cholesterol related disorder as disclosed.

In an embodiment of the methods disclosed herein, the anti-lipemic drug is preferably disposed as a liposome formulation. In this example, the liposome formation can be compatible for hepatic administration in accordance with standard practice. Also in this example, the liposome formulation can be administered to the liver or associated organ in a human patient according to standard medical techniques involving, e.g., oral, intramuscular, intraperitoneal, administration via a stent or related implementation. Particular routes of administration are provided below.

Other aspects of the invention are discussed below.

BRIEF DESCRIPTION OF THE DRAWINGS

FIGS. 2A and 2B are graphs illustrating effects of TNF-$\alpha$, sphingomyelinase, and $C_2$-ceramide on the kinetics of SREBP-1 maturation. 2A) kinetics of SREBP-1 maturation, 2B) ratio of immature/mature SREBP-1 versus time.

FIGS. 6A–6D are representations of gels showing results of electrophoretic mobility shift assays.

FIG. 11 is a drawing showing a nucleotide sequence (SEQ ID NO:1) of isolated cDNA encoding human N-SMase.

FIG. 12 is a drawing illustrating the deduced amino acid sequence (SEQ ID NO:2) of human N-SMase.

FIG. 13 is a drawing showing examples of particular anti-lipemic drugs, target organs and particular actions of the drugs.

FIGS. 15A–B are drawings showing (15A) sphingomyelin and (15B) C-2 ceramide and dihydro-C-2 ceramide. The 3-hydroxyl group and 4, 5 trans carbon-carbon double bond in the sphingosine backbone are indicated by arrows.

DETAILED DESCRIPTION OF THE INVENTION

Figure 1:
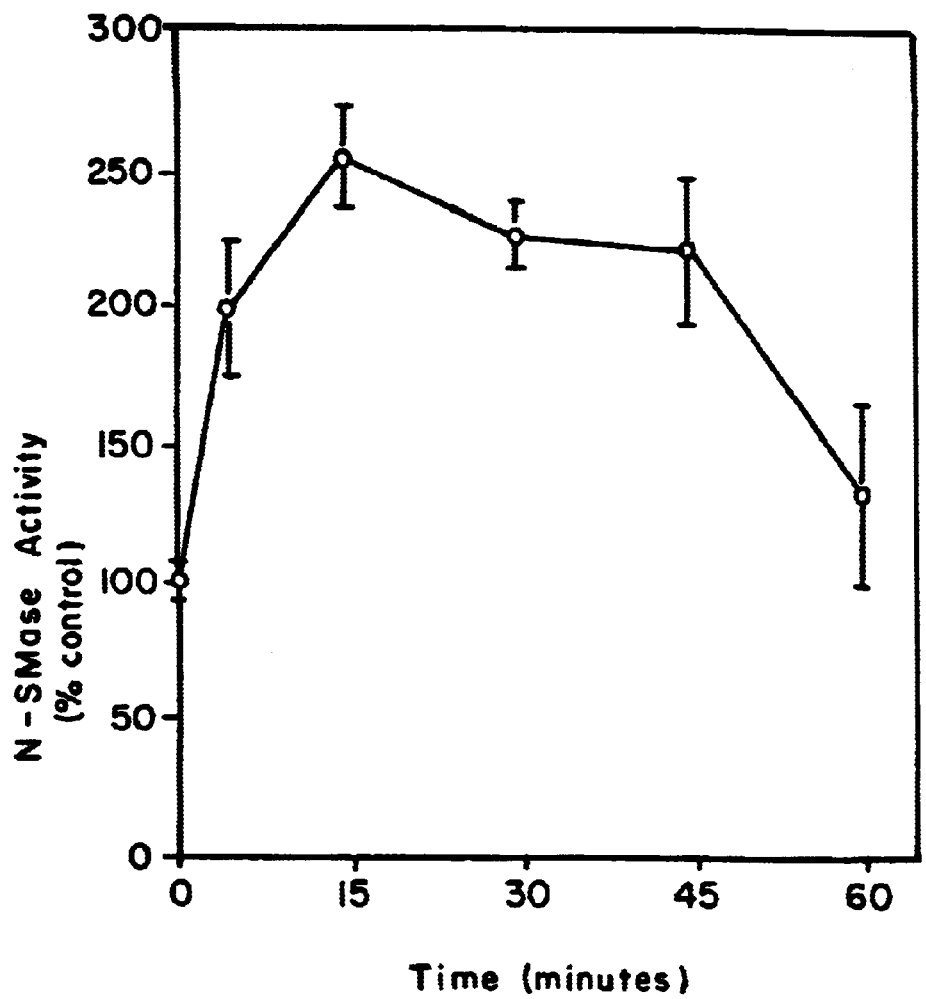
FIG. 1 is graph showing effect of TNF-$\alpha$ on neutral sphingomyelinase (N-SMase) activity.

As discussed, the invention relates to anti-lipemic drugs and methods for using same to stabilize or reduce serum cholesterol level in a human patient or other subject mammal. Preferred anti-lipemic drugs generally include one identified effector of the SREBP-1 protein associated with one identified serum cholesterol inhibitor. More preferred are anti-lipemic drugs in which the effector and inhibitor components are specifically covalently linked together as a single formulation.

The term "anti-lipemic drug" is used herein to refer generically to a composition of this invention, preferably a specific synthetic or semi-synthetic drug, which has dual capacity to modulate serum cholesterol levels, ie, by modulating the LDL receptor and stabilizing or reducing serum cholesterol levels in the subject mammal. Preferred is an anti-lipemic drug with demonstrated capacity to increase LDL receptor levels and to reduce serum cholesterol levels as determined by specific in vitro and in vivo assays described below. As discussed below, capacity to reduce serum cholesterol levels by the inhibitor component is generally mediated by modulation of HMG CoA reductase, typically by inhibiting that enzyme sufficient to reduce serum cholesterol. As also discussed, the effector portion preferably increases production of the LDL receptor.

The anti-lipemic drugs disclosed herein can be made by recognized methods known in the field. For example, methods for making specific sphingolipids and especially ceramide and ceramide-related compounds have been disclosed in co-pending U.S. patent application Ser. No. 08/998,262 entitled "Methods for Treatment of Conditions Associated with Lactosylceramide" filed on Dec. 24, 1997, now issued as U.S. Pat. No. 5,972,928 on Oct. 26, 1999, the disclosure of which is incorporated herein by reference. See also Abe, A. et al., (1992) *J. Biochem.* 111:191–196; Inokuchi, J. et al. (1987) *J. Lipid Res.* 28:565–571; Shukla, A. et al. (1991) *J. Lipid Res.* 32:73; Vurmam, R. R. et al., (1980) *Chem. and Physics of Lipids* 26:265; Carson, K. et al., (1994) *Tetrahedron Lets.* 35:2659; and Akira, A. et al., (1995) *J. Lipid Research* 36:611.

More specific anti-lipemic drugs of this invention include as covalently linked components the effector and the serum cholesterol inhibitor. However for some applications other anti-lipemic drugs can be appropriate such as those including non-covalently linked components. Examples include those drugs provided as essentially co-administered formulations.

The molecular weight of a particular anti-lipemic drug will vary depending, e.g., on the specific SREBP-1 effector and serum cholesterol inhibitor chosen and the number of effectors and inhibitors making up the drug. However in most cases the anti-lipemic drug will have a molecular weight of less than about 10,000 kD to 35,000 kD particularly when the effector molecule is a protein or polypeptide sequence such as the N-SMase sequences or fragments thereof disclosed herein. Molecular weights will generally be significantly lower, e.g., between from about 100 kD to 1000 kD, preferably between from about 200 kD to 500 kD when the effector is a sphingomyelin or related molecule. Methods for determining the molecular weight are known and include standard molecular sizing methods such as SDS polyacrylamide gel electrophoresis.

Illustrative examples of specific anti-lipemic drugs in accord with this invention are shown in FIG. 13. FIG. 13 particularly shows use of combinations of SREBP-1 maturation upregulators (effectors) ceramide, N-SMase, and various lipid lowering molecules; HMG CoA-reductase inhibitors (statins) in various human pathologies.

An "effector" of the LDL receptor and particularly the SREBP-1 protein is a molecule, usually an amino acid sequence, lipoprotein, lipid or like molecule with demonstrated capacity to modulate the LDL receptor and specifically maturation of the SREBP-1 protein as determined by the standard SREBP-1 maturation assay described below. Illustrative effectors are provided in the Examples and FIG. 7.

Figure 14:
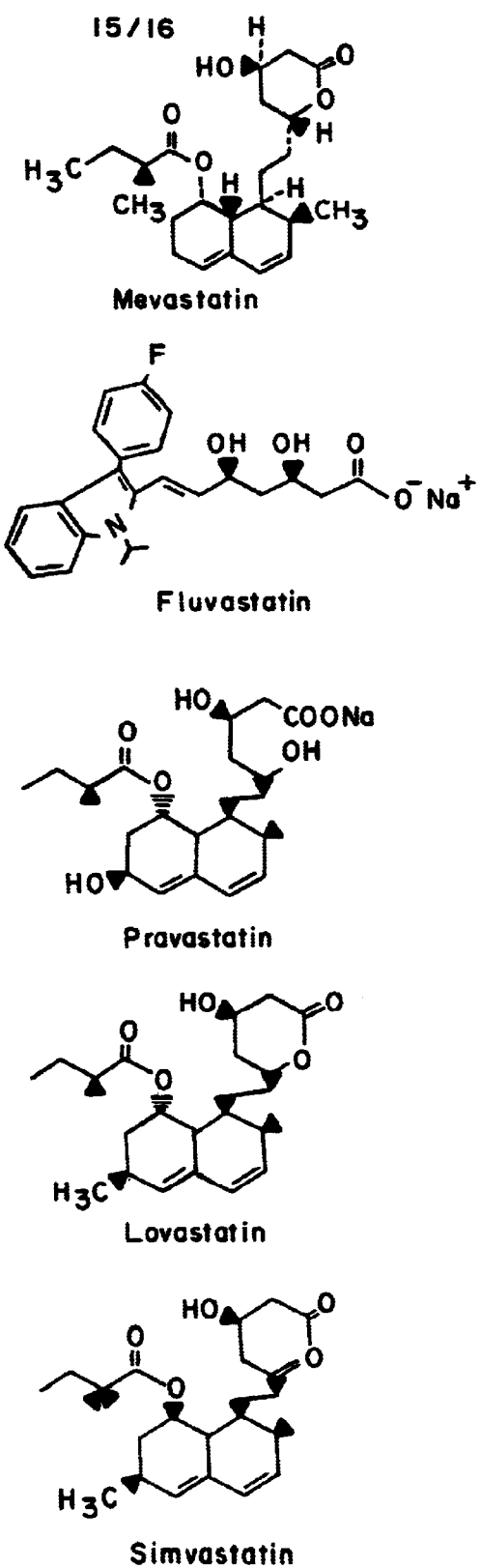
FIG. 14 is a drawing showing chemical structures for specific serum cholesterol inhibitors mevastatin, fluvastatin, pravastatin, lovastatin and simvastatin. The inhibitors are HMG-CoA reductase inhibitors. Fluvastatin is an entirely synthetic mevalonolactone derivative. Remaining reductase inhibitors are fungal compactin derivatives based on a hydronapthalene ring.

A "serum cholesterol inhibitor" as that term is used herein generally refers to a recognized compound capable of reducing serum cholesterol levels in a subject mammal and especially a human patient. Preferred serum cholesterol inhibitors particularly interfere with cholesterol biosynthesis and especially HMG CoA-reductase activity, e.g., in the liver. More preferred serum cholesterol inhibitors are readily available commercially and include mevastatin, fluvastatin, pravastatin, lovastatin and simvastatin. See FIG. 14 and the discussion below.

It has been unexpectedly found that TNF-α significantly stimulates maturation of SREBP-1 in cells through action of the N-SMase. That is, we have found that TNF-α is capable of inducing SREBP-1 maturation in a time and dose dependent manner. This induction was consistent with the kinetics of TNF-α mediated activation of neutral sphingomyelinase (N-SMase). Antibodies to N-SMase inhibited TNF-α induced SREBP-1 maturation suggesting that N-SMase is a necessary component of this signal transduction pathway. Ceramide, a product of sphingomyelin hydrolysis, was also found to be capable of inducing SREBP-1 maturation. Without wishing to be bound to theory, it appears that the mature form of SREBP-1 generated by TNF-α, sphingomyelinase or ceramide treatment translocates to the nucleus and binds the sterol regulatory element (SRE). This is believed to promote transcription of the gene upstream of the SRE. See FIG. 7 for a schematic outline of these findings. It further appears that effectors of the SREBP-1 stimulate the LDL receptor, particularly by enhancing SREBP-1 maturation, thereby stabilizing or reducing serum cholesterol in the subject mammal.

Therapeutic methods of the invention generally comprise administration of a therapeutically effective amount of at least one and typically one anti-lipemic drug as disclosed herein to a subject mammal such as a primate and especially a human patient in such treatment. The therapeutic treatment methods more specifically include administration of an effective amount of the anti-lipemic drug to a subject, particularly a mammal such as a human in need of such treatment for an indication disclosed herein.

Typical subjects of interest include those suffering from, suspected of suffering from, or susceptible to the conditions, disorders or diseases disclosed herein, e.g., hyperlipoproteinemia including hypercholesterolemia, stroke, obesity including compulsive eating disorders, cardiac disease including atherosclerosis, cerebral atherosclerosis, cholesteryl ester storage disorder, liver disease including organ transplantation failure and cirrhosis; diseases of the biliary system, and viral infection particularly those infections facilitating encephalitis or related disorders. More specific disclosure relating to these and other cholesterol related diseases including accepted methods for screening and diagnosing these disorders have been reported. See e.g., Brown, M. S. and Goldstein, J. L. (1993), supra and references cited therein.

A variety of specific anti-lipemic drugs can be employed in the present invention and particularly in the treatment methods described. Routine testing, e.g., in a standard in vitro assay optionally combined with another in vitro and/or in vivo assay, can in most instances readily identify suitable anti-lipemic drugs exhibiting desired selectivity and activity with respect to the target disorder or disease. As noted, preferred anti-lipemic drugs feature a specific effector of the SREBP-1 protein such as those effectors identified in the Examples including N-SMase or an effective fragment thereof; a sphingolipid and especially ceramide, a caspase, e.g., cpp32 protein (caspase-3), or an effective fragment thereof; as well as other specific effectors discussed herein.

Additionally specific effectors are disclosed in the Examples and discussion which follows. For example, one anti-lipemic drug of this invention includes covalently linked in sequence: 1) an SREBP-1 effector comprising a chemically reactive group; and 2) a serum cholesterol inhibitor such as those disclosed herein including another chemically reactive group capable of specifically binding generally by covalent linkage to the reactive group of the effector. Optionally, the anti-lipemic drug further includes a bifunctional spacer, e.g., a heterobifunctional spacer, covalently linked between 1) and 2).

A more preferred anti-lipemic drug includes covalently linked in sequence: 1) a sphingolipid and especially sphingomyelin or ceramide; and 2) a specific serum cholesterol inhibitor as disclosed herein. In this embodiment, the ceramide is preferably naturally-occurring and can be any one of C-2, C-4, C-6 or C-8 ceramide. In embodiments in which the SREBP-1 effector is ceramide, the reactive group will typically be the C-3 group of ceramide. Preferred are serum cholesterol inhibitors that include a suitably chemically reactive hydroxyl (—OH) group, e.g., fluvastatin, simvastatin, lovastatin, pravastatin, mevinolin (compactin), or atorvastatin. Optionally, the anti-lipemic drug may include a bifunctional spacer covalently linked between 1) and 2), i.e., providing a covalent bond between the C-3 group and the hydroxyl group.

Chemical structures for sphingomyelin and specific ceramides (C-2 ceramide, dihydro-C-2-ceramide) are shown in FIGS. 15A and 15B.

Also preferred is an anti-lipemic drug that includes covalently linked in sequence: 1) the neutral sphingomyelinase (N-SMase) or the effective fragment thereof, and 2) a specific serum cholesterol inhibitor as disclosed herein. In this embodiment in which the SREBP-1 effector is N-SMase or the fragment, the chemically reactive group will be a suitable amide bond. Preferred are serum cholesterol inhibitors that include a suitably chemically reactive hydroxyl (—OH) group, e.g., fluvastatin, simvastatin, lovastatin, pravastatin, mevinolin (compactin), or atorvastatin. Optionally, the anti-lipemic drug may include a bifunctional spacer and particularly a heterobifunctional spacer covalently linked between 1) and 2). Suitable linker sequences are known in the field and generally include chemically reactive groups on each end of a suitable polymeric sequence such as an amino acid sequence.

Illustrative N-SMase and fragments thereof for use in accord with this invention are provided in the examples and discussion which follow as well as the co-pending U.S. application Ser. No. 08/774,104 entitled "Recombinant N-SMases and Nucleic Acids Encoding Same" filed on Dec. 24, 1996, now issued as U.S. Pat. No. 5,919,687 on Jul. 6, 1999, the disclosure of which is incorporated herein by reference.

In particular, a preferred neutral sphingomyelinase (N-SMase) is encoded by a sequence having at least 70%, 80%, 90% or 95% sequence identity to the sequence shown in FIG. 12 (SEQ ID NO:1) or the complement thereof. A preferred fragment of the N-SMase includes a sequence having at least 70%, 80% or 90% sequence identity to nucleotides 862 to 1414 of SEQ ID NO:1 or the complement thereof. More specifically preferred is an N-SMase fragment that consists of nucleotides 862 to 1414 of SEQ ID NO:1 or the complement thereof. Methods for determining nucleotide sequence identity are known in the field and include use of well-known computer assisted programs such as FASTA and BLAST. See S. Altschul et al. *J. Mol. Biol.*, 215:403 (1990); and S. Altschul et al. *Nuc. Acids Res.*, 25: 3389–3402 (1997)for disclosure relating to the BLAST and related programs.

The term "effective fragments" as it relates to preferred N-SMase nucleotide fragments is used herein to refer to a specific nucleotides having significant activity in the standard in vitro SREBP-1 maturation assay described below. A specifically preferred example of an effective fragment of the N-SMase is nucleotides 862 to 1414 of SEQ ID NO:1.

As discussed, preferred anti-lipemic drugs of this invention exhibit significant activity in a standard SREBP-1 maturation assay. Preferably, the drug exhibits at least about 2 fold, preferably between about 2 to 10 fold, and more preferably from about 2 to 5 fold as determined by the assay. A preferred assay generally involves:

a) culturing suitable cells, e.g., HH-25 cells, in medium and adding the anti-lipemic drug for between from about 2 to 60 minutes, preferably between from about 10 to 30 minutes with about 15 minutes being generally preferred, typically followed by washing; and b) detecting mature SREBP-1 (i.e., proteolytically cleaved) and precursor SREBP-1 by performing Western immunoblotting with an anti-SREBP-1 antibody such as those described below. In general, mass of the mature form of SREBP-1 can quantitatively determined vs. the precursor form. Presence of that mature form is indicative of SREBP-1 maturation and proteolysis. More specific methods for performing the assay are provided in the Examples which follow. Typically suitable control cells are included as a reference which cells are not exposed to the drug.

As also discussed, preferred anti-lipemic drugs of this invention exhibit good activity in a Northern blot assay for detecting and preferably quantifying LDL receptor mRNA. Additionally preferred anti-lipemic drugs are capable of increasing LDL receptor mRNA levels by at least about 10% and preferably at least from between about 20% to 50% as determined by the Northern blot assay or related mRNA detection assay. Methods for performing Northern blot assays are generally known and have been described, e.g., in Sambrook et al. in *Molecular Cloning: A Laboratory Manual* (2d ed. 1989); and Ausubel et al., *Current Protocols in Molecular Biology*, John Wiley & Sons, New York, 1989.

Suitable probes for detecting LDL mRNA are generally available and include cloned sequences of the human LDL receptor or related mammalian sequence available from Genbank. Information about Genbank can be obtain from the National Library of Medicine, 38A, 8N05, Rockville Pike, Bethesda, Md. 20894. Genbank is also available on the internet through the National Center for Biotechnology Information (NCBI). See generally Benson, D. A. et al. (1997) *Nucleic Acids Res.* 25:1 for a more complete description of Genbank.

An exemplary Northern blot assay for detecting and optionally quantitating LDL receptor mRNA levels is discussed below.

Preferred inhibitors of the HMG CoA reductase generally reduce or block synthesis of cholesterol in the liver, thereby facilitating compensatory reactions that can lead to a reduction in plasma LDL. A preferred assay for measuring this phenomenon is the standard HMG CoA reductase assay. As mentioned previously preferred anti-lipemic drugs of this invention exhibit an $ID_{50}$ of between from about 20%, 30%, 40%, 50%, 60%, 70%, or 80% to about 90%, preferably between from about 30% to 50% as determined in the HMG CoA reductase assay. The standard HMG CoA reductase assay has been disclosed by Brown et al. (1978) *J. Biol. Chem.* 253: 1121. In this assay cultured human fibroblasts respond to an inhibition of the reductase by accumulating increased amounts of the enzyme when compared to a suitable control.

As also discussed additionally preferred anti-lipemic drugs are capable of reducing serum cholesterol as determined by a standard cholesterol assay. The drug preferably registers at least from about 5% or 10% to 20%, 30%, 40% or 50% decrease, preferably at least about 30% to 50% decrease as determined by the assay. A preferred assay for measuring LDL cholesterol is commercially available from Sigma (St. Louis, Mo.) and involves immunological separations. See also the National Cholesterol Education Program (NCEP) for information relating to acceptable cholesterol levels in humans.

A "high" or "high risk" cholesterol level or related term is defined herein as from between about 200 to 240 mg/dl (mM) cholesterol with a level greater than or equal to 240 mg/dl (mM) cholesterol being more generally understood to be indicative of high serum cholesterol. A normal serum cholesterol level is defined herein as being less than about 200 mg/dl (mM). For specific disclosure relating to conducting cholesterol tests see Brown, M. S. and Goldstein, J. L. supra, discussing the Guidelines of the NCEP Report of 1988.

Accordingly, "stabilization" or "reduction" of serum cholesterol as those terms are used herein will be understood to mean manifestation of a normal or near normal serum cholesterol level in the subject mammal. Also, a suitable control mammal in accord with this invention will preferably have a normal or near normal serum cholesterol level as determined by standard serum cholesterol tests.

Additional methods of this invention include modulating SREBP-1 levels in a mammal in which the method includes administering to the mammal a therapeutically effective amount of at least one and typically one of the anti-lipemic drugs disclosed herein. Typically, modulation of the SREBP-1 is evaluated by determining maturation of the protein as determined by the SREBP-1 maturation tests described in the Examples below.

The present invention also provides methods for modulating SREBP-1 levels in a mammal in which the method includes administering to the mammal a therapeutically effective amount of at least one and preferably one of the anti-lipemic drugs disclosed herein. In this embodiment, the SREBP-1 effector is neutral sphingomyelinase (N-SMase) or a therapeutically effective fragment thereof; or a sphingolipid. As discussed, modulation of the SREBP-1 is typically evaluated by determining maturation of the protein as determined by the SREBP-1 maturation tests described in the Examples below. A preferred assay is the SREBP-1 proteolysis assay described below in the Examples.

Methods of this invention can be performed in vitro or in vivo using acceptable primary, cultured or immortalized cells such as those disclosed herein. Generally, these cells will be capable of exhibiting SREBP-1 maturation as defined herein including the HH-25 human hepatocytes described below. Methods for testing anti-lipemic drugs of interest and especially for use in human patient will preferably be conducted in vivo and may involve use of a suitable animal model depending on the method used. In this example, the model can be a suitable animal model such as those discussed previously. Alternatively, the methods can be performed on a suitable primate such as a human patient. Preferred is a human patient has been diagnosed as having, is suspected of having, or is susceptible to a cholesterol related disorder as defined above.

In embodiments in which the human patient is susceptible to one or more cholesterol related disorders, that susceptibility can be related to a genetic or environmental pre-disposition to the cholesterol related disorder. Methods for determining such pre-disposition are known in the field and include genetic testing. See Brown, M. S. and Goldstein, J. L. (1993) supra.

The invention thus provides methods for treating inappropriate (i.e. high) serum cholesterol levels as well as a disorder or condition associated therewith. In general, the methods include administration of a therapeutically effective amount of one or more anti-lipemic compounds of this invention to a subject mammal, particularly a human, suffering from or susceptible to the high serum cholesterol levels. Additionally contemplated is use of the present anti-lipemic compounds as prophylactic drugs to prevent development of or reduce the severity of inappropriate serum cholesterol levels.

Compounds of the invention will be especially useful to a human patient who has or is suspected of having a cholesterol related disease, disorder or condition as defined herein. Compounds of the invention will be particularly useful in lowering serum cholesterol to normal or near normal levels in human patients. Specific examples of diseases which may be treated in accordance with the invention include hyperlipoproteinemia, stroke, cardiovascular disease and especially atherosclerosis as well as other specific disorders of conditions mentioned herein.

Without wishing to be bound by theory, it is believed the multiple and distinct covalently linked compounds of this invention (i.e. at least one identified anti-lipemic drug in combination with at least one identified SREBP-1 effector) can significantly enhance efficacy of the anti-lipemic drug, e.g., by increasing synthesis of LDL receptor in subject cells.

Moreover, by virtue of the covalent linkage, the conjugates of the invention present the anti-lipemic drug and the SREBP-1 effector to the subject cell essentially simultaneously, an effect that may not be readily achieved by administering the same compounds in a drug "cocktail" formulation without covalently linking the compounds.

It also has been reported that treatment with one drug can in turn sensitize a patient to another drug. Accordingly, the essentially simultaneous presentation to the subject cell of an anti-lipemic drug and SREBP-1 effector via a conjugate of the invention may enhance drug activity, e.g., by providing synergistic results and/or by enhancing production of LDL receptors. Particular SREBP-1 effectors of interest include sphingomyelin and especially ceramide and related compounds. Also preferred is N-SMase as well as therapeutically effective fragments of that enzyme.

Administration of compounds of the invention may be made by a variety of suitable routes including oral, topical (including transdermal, buccal or sublingal), nasal and parenteral (including intraperitoneal, subcutaneous, intravenous, intradermal or intramuscular injection) with oral or parenteral being generally preferred. It also will be appreciated that the preferred method of administration and dosage amount may vary with, for example, the condition and age of the recipient.

Compounds of the invention may be used in therapy in conjunction with other medicaments such those with recognized pharmacological activity to lower concentrations of plasma lipoproteins. See Brown, M. S. and Goldstein, J. L. supra. Exemplary medicaments are recognized serum cholesterol inhibitors (i.e. reported to inhibit HMG CoA reductase) such as Lescol™ (fluvastatin from Sandoz Pharmaceuticals), Mevacor™ and Zocor™ (simvastatin and lovastatin, respectively, from Merck & Co.), Pravachol™ (pravastatin from Bristol-Myers Squibb Co.) and mevinolin (compactin).

The compounds of this invention may be used alone or in combination with other accepted anti-lipemic therapies including those implementing use of fibric acids, e.g., gembibrozil, clofibrate, fenofibrate, ciprofibrate or bezafibrate; bile acid-binding resins such as cholestyramine or colestipol; and probucol. The compounds of this invention can be administered before, during or after such therapies as needed.

While one or more compounds of the invention may be administered alone, they also may be present as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

For parenteral application, particularly suitable are solutions, preferably oily or aqueous solutions as well as suspensions, emulsions, or implants, including suppositories. Ampules are convenient unit dosages.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

Therapeutic compounds of the invention also may be incorporated into liposomes. The incorporation can be carried out according to known liposome preparation procedures, e.g. sonication and extrusion. Suitable conventional methods of liposome preparation are also disclosed in e.g. A. D. Bangham et al., *J. Mol. Biol.*, 23:238–252 (1965); F. Olson et al., *Biochim. Biophys. Acta*, 557:9–23 (1979); F. Szoka et al., *Proc. Nat. Acad. Sci.*, 75:4194–4198 (1978); S. Kim et al., *Biochim. Biophys. Acta*, 728:339–348 (1983); and Mayer et al., *Biochim. Biophys. Acta*, 858:161–168 (1986).

The liposome may be made from one or more of the conjugates discussed above alone, or more preferably, in combination with any of the conventional synthetic or natural phospholipid liposome materials including phospholipids from natural sources such as egg, plant or animal sources such as phosphatidylcholine, phosphatidylethanolamine, phosphatidylglycerol, sphingomyelin, phosphatidylserine or phosphatidylinositol. Synthetic phospholipids also may be used e.g., dimyristoylphosphatidylcholine, dioleoylphosphatidylcholine, dioleoylphosphatidycholine and corresponding synthetic phosphatidylethanolamines and phosphatidylglycerols. Cholesterol or other sterols, cholesterol hemisuccinate, glycolipids, 1,2-bis(oleoyloxy)-3-(trimethyl ammonio)propane (DOTAP), N-[1-(2,3-dioleoyl)propyl]-N,N,N-trimethylammonium chloride (DOTMA), and other cationic lipids may be incorporated into the liposomes. The relative amounts of the one or more compounds and additives used in the liposomes may vary relatively widely. Liposomes of the invention suitably contain about 60 to 90 mole percent of natural or synthetic phospholipid; cholesterol, cholesterol hemisuccinate, fatty acids or cationic lipids may be used in amounts ranging from 0 to 50 mole percent; and the one or more therapeutic compounds of the invention may be suitably present in amounts of from about 0.01 to about 50 mole percent.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, for treatment of a lipid related disease as disclosed herein and particularly hyperlipoproteinemia, stroke, coronary heart disease and especially atherosclerosis, a suitable effective dose of one or more compounds of this invention will be in the range of from 0.01 to 100 milligrams per kilogram of bodyweight of recipient per day, preferably in the range of from 0.1 to 50 milligrams per kilogram bodyweight of recipient per day, more preferably in the range of 1 to 20 milligrams per kilogram bodyweight of recipient per day. The desired dose is suitably administered once daily, or several sub-doses, e.g. 2 to 5 sub-doses, are administered at appropriate intervals through the day, or other appropriate schedule.

A preferred dose for many compounds of this invention will be in the range of those dosages accepted for identified HMG CoA reductase inhibitors with lower than that range being preferred for many patients. See the *Physicians' Desk Reference*, supra for more specific information relating to recommended doses for HMG CoA reductase inhibitors with anti-lipemic activity.

In another aspect, the invention also provides methods for detecting an effector of the sterol regulatory element binding protein-1 (SREBP-1). In one embodiment, the method includes the steps of:

a) providing a population of cells capable of expressing SREBP-1, b) contacting the cells with a candidate effector in an amount sufficient to induce maturation of the SREBP-1, c) culturing the cells in medium; and d) detecting maturation of the SREBP-1 as indicative of the effector of the SREBP-1.

Figure 7:
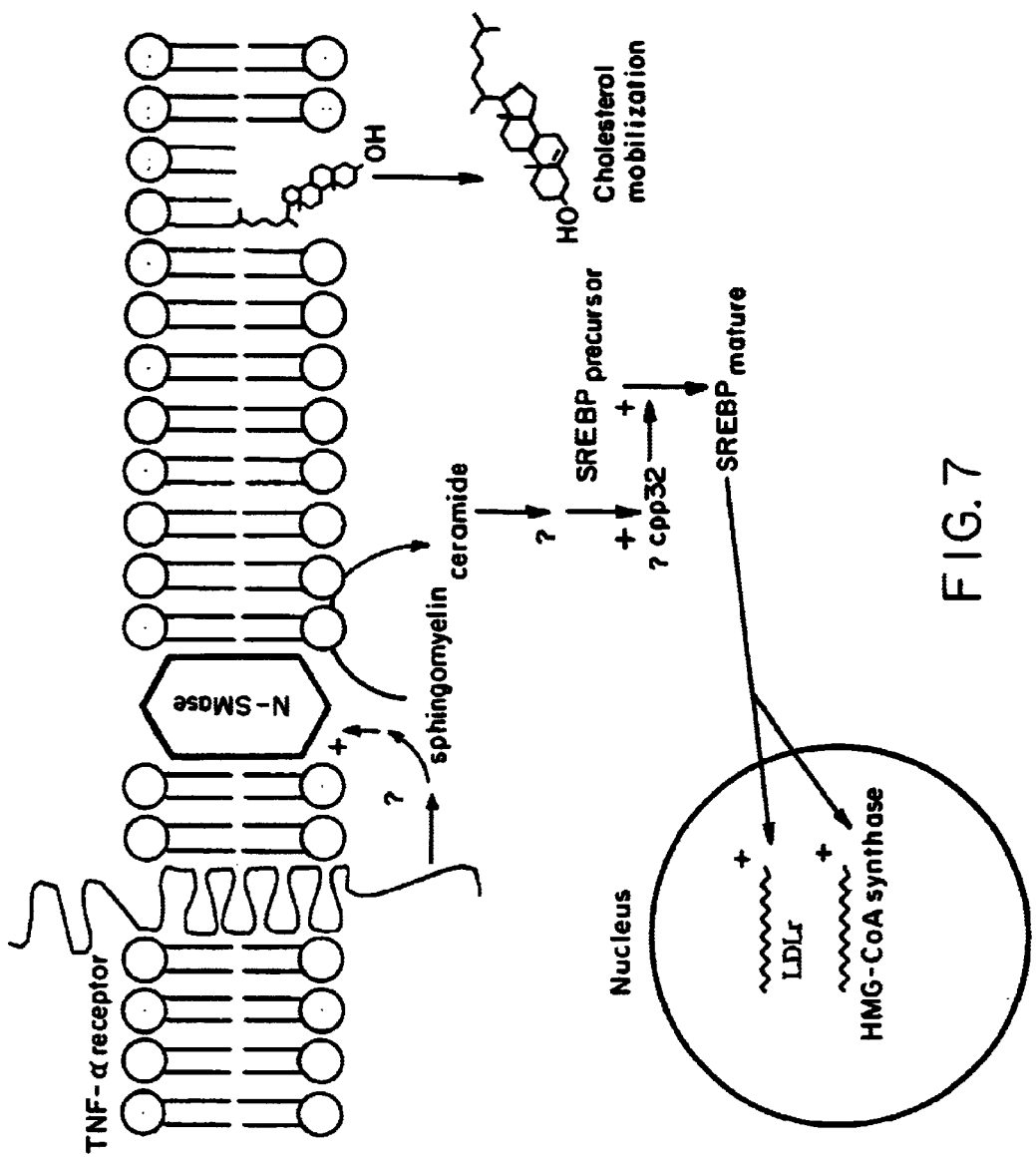
FIG. 7 is a model showing how TNF-$\alpha$ induces SREBP-1 proteolysis(maturation) and mobilizes membrane cholesterol in human hepatocytes. Effectors of the LDL receptor and particularly SREBP-1 are shown schematically.

Illustrative effectors for use in the method are include those specifically described in the Examples and FIG. 7, e.g., tumor necrosis factor (TNF-α), neutral sphingomyelinase (N-SMase) or an effective fragment thereof, sphingomyelin, ceramide, cpp32, or cholesterol. See also FIG. 13.

The invention also includes a method for detecting an effector of LDL receptor biosynthesis. In one embodiment, the method includes:

a) providing a population of cells responsive to ceramide and capable of expressing SREBP-1, b) contacting the cells with a candidate effector in an amount sufficient to induce maturation of the SREBP-1, c) culturing the cells in medium; and d) detecting biosynthesis of the LDL receptor as being indicative of the effector of the LDL receptor.

In one embodiment of the method, illustrative candidate effectors of the LDL receptor is tumor necrosis factor (TNF-α), neutral sphingomyelinase (N-SMase) or an effective fragment thereof; sphingomyelin, ceramide, cpp32, or cholesterol.

Also provided by the present invention is a method for determining therapeutic capacity of an effector of SREBP-1 for treating a cholesterol related disease in a mammal. In one embodiment, the method includes:

a) providing a population of cells capable of expressing SREBP-1, b) contacting the cells with a candidate compound in an amount sufficient to induce maturation of the SREBP-1, c) culturing the cells in medium; and d) detecting maturation of the SREBP-1 as indicative of the therapeutic capacity of the effector in treating the disease.

The present invention also provides methods for determining therapeutic capacity of any one of the anti-lipemic drugs disclosed herein for treating a cholesterol related disease in a mammal. In one embodiment, the method includes:

a) providing a population of cells capable of expressing SREBP-1, b) contacting the cells with the anti-lipemic drug in an amount sufficient to induce maturation of the SREBP-1, c) culturing the cells in medium; and d) detecting maturation of the SREBP-1 as indicative of the therapeutic capacity of the anti-lipemic drug in treating the disease.

Also provided herein are methods for determining therapeutic capacity of one or more of the anti-lipemic drugs disclosed herein using a Watanabe heritable hyperlipidemic rabbit or apolipoprotein and negative mouse as an animal model. In one embodiment, the method includes:

a) administering at least one of the anti-lipemic drugs to the rabbit or mouse in an amount sufficient to reduce serum cholesterol levels by at least from about 10 to 20% as determined by a standard cholesterol assay; and b) detecting the serum cholesterol reduction in the rabbit or mouse as being indicative of the therapeutic capacity of the anti-lipemic drug to treat the cholesterol related disease.

Methods of this invention can optionally include monitoring LDL receptor activity as being indicative of the effector of the SREBP-1. In this embodiment, the receptor activity can be suitably monitored and quantified if desired by one or a combination of standard strategies. For example, a variety of specific methods have been reported to monitor LDL receptor activity and particularly to detect increases or decreases in the level of LDL receptors. See Brown, M. S. and Goldstein, J. L. (1993), supra and references cited therein for several immunological and molecular approaches. A preferred method is the standard LDL receptor Northern blot assay disclosed herein.

Suitable cells for use in the methods of this invention are described in the Examples which follow.

Preferred are cells which include SREBP-1 and are capable of SREBP-1 maturation as determined by the standard assay described herein. More preferred are cells responsive to an increase or decrease in intracellular sphingolipid and especially ceramide or a related compound such as human hepatocytes as provided in the Examples below.

Suitable effectors or candidate compounds for use with the methods can be those specific compounds described herein neutral sphingomyelinase (N-SMase) or an effective fragment thereof; sphingomyelin, ceramide, cpp32, or cholesterol. An illustrative neutral sphingomyelinase (N-SMase) is encoded by a sequence having at least 70%, 80%, or 90% sequence identity to the sequence represented by SEQ ID NO:1 or complement thereof. Alternatively, the effective fragment of the neutral sphingomyelinase (N-SMase) can include a sequence having at least 70%, 80% or 90% sequence identity to nucleotides 862 to 1414 of SEQ ID NO:1 or complement thereof.

It is preferred that the anti-lipemic drugs as well as components thereof (e.g., ceramide) be substantially pure. That is, the drugs will be present in at least 90 to 95% homogeneity (w/w). Anti-lipemic drugs having at least 98 to 99% homogeneity (w/w) are most preferred for many pharmaceutical, clinical and research applications. Once substantially purified the drug should be substantially free of contaminants for therapeutic applications. Once purified partially or to substantial purity, the drugs can be used therapeutically, or in performing preferred in vitro or in vivo assays as disclosed herein. Substantial purity can be determined by a variety of standard techniques such as chromatography and gel electrophoresis.

The Examples 1–8 below illustrate that TNF-α is capable of inducing SREBP-1 proteolysis independent of the presence of sterols. Exogenously supplied sphingomyelinase and ceramide are also capable of inducing SREBP-1 proteolysis in a time and dose dependent manner. The kinetics of SREBP-1 maturation is consistent with those of neutral sphingomyelinase activation by TNF-α. Further, SREBP-1 maturation can be blocked with anti-N-SMase antibodies indicating that neutral sphingomyelinase is necessary for TNF-α induced, sterol independent SREBP-1 cleavage. The product of sterol independent SREBP-1 proteolysis is capable of nuclear translocation and binds to the sterol regulatory element.

All documents mentioned herein are incorporated herein by reference.

The following abbreviations are used throughout this disclosure including the following examples as needed:

N-SMase, neutral sphingomyelinase; LDLr, Low Density Lipoprotein receptor; SREBP-1, Sterol Regulatory Element Binding Protein-1. Numbered citations are listed in numerical order below.

EXAMPLE 1

The effect of TNF-α on Neutral Sphingomyelinase Activity

Neutral sphingomyelinase activity increased rapidly with the addition of TNF-α. See FIG. 1. A maximal 2.5 fold increase in activity was observed 15 minutes after TNF-α was added to the cells. The gradual return of N-SMase activity to control levels within 1 hour contrasted the rapid onset of activation and is reflected in the asymmetric kinetic profile observed.

FIG. 1 illustrates the effect of TNF-α on neutral sphingomyelinase activity and is explained in more detail as follows: Confluent cultures of HH-25 cells were washed once with PBS and incubated in serum free media for 30 minutes prior to the addition of TNF-α (10 ng/ml). At the indicated time, cells were harvested in PBS, pelleted and frozen. Cells were subsequently lysed as described in materials and methods. N-SMase assays were performed in duplicate as described. Error bars represent ±one standard deviation from the mean.

EXAMPLE 2

Kinetics of SREBP-1 Proteolysis

Sterol independent SREBP-1 maturation in response to TNF-α closely paralleled the kinetics of TNF-α induced N-SMase activation. The mass of the mature form of SREBP-1 was found to increase 2 fold after 5 minutes and 3 fold after 15 minutes of incubation with TNF-α. See FIG. 2A. The amount of mature SREBP-1 returned to control levels within one hour. This effect could not be recapitulated with EGF or PDGF treatment. The increase in mature SREBP-1 levels was accompanied by a concomitant decrease in the intensity of the band corresponding to the precursor form of SREBP-1. See FIG. 2B. After 60 minutes of treatment significantly less precursor SREBP-1 was visible.

To incorporate the observed increase in mature SREBP-1 and the concomitant decrease in precursor SREBP-1 into a single variable, the ratio of precursor SREBP-1 to mature was plotted. See FIG. 2B. A maximal 1.5 fold decrease in the precursor to mature ratio occurred 45 minutes after TNF-α was added to the media. The decrease in precursor to mature ratio was more pronounced in the initial 30 minutes of treatment. This is also consistent with the kinetics of TNF-α induced N-SMase activation.

Figure 2A:
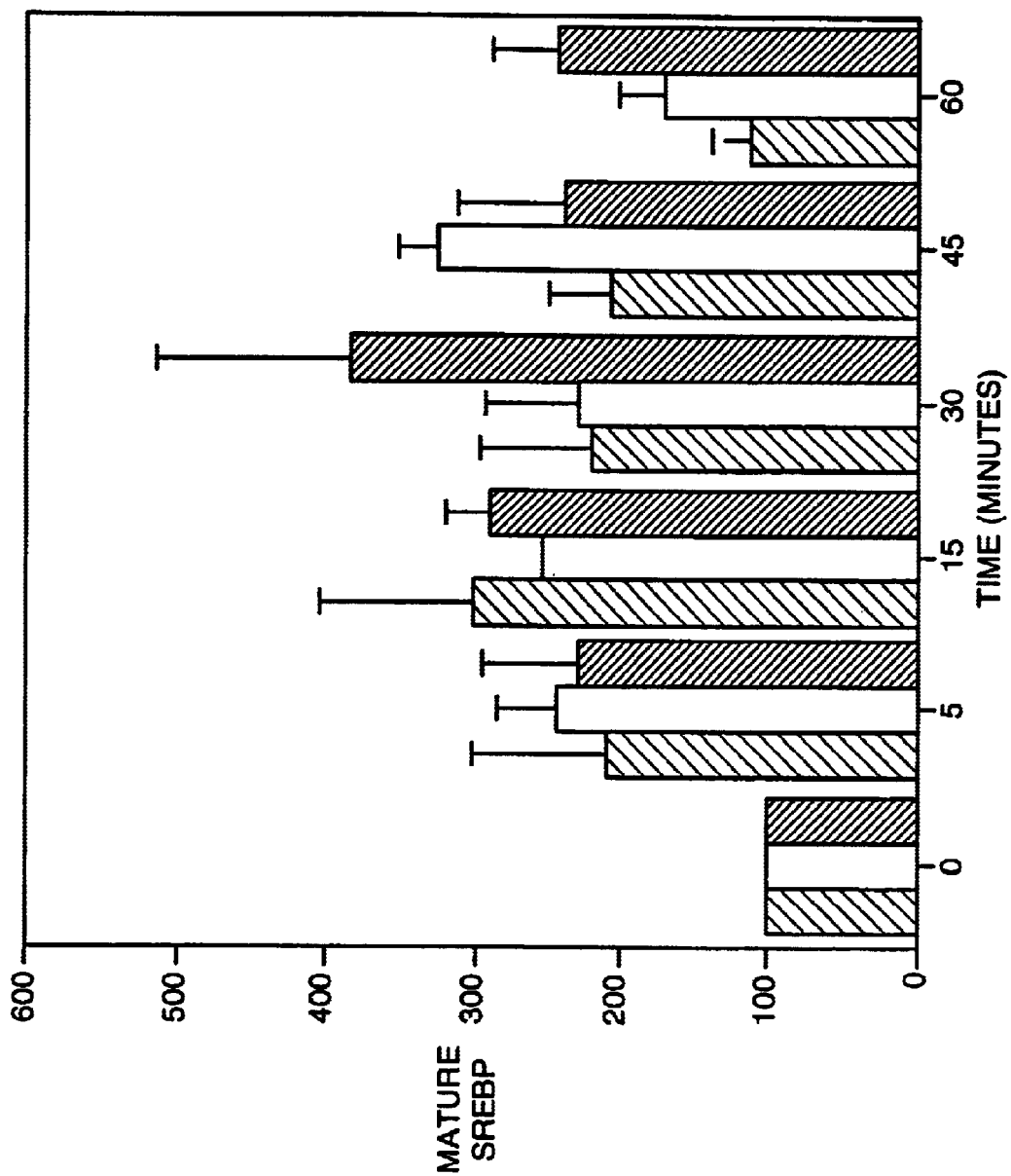

To explore the possibility that plasma membrane sphingomyelinase was involved in the signal transduction pathway leading to SREBP-1 proteolysis, cells were treated with exogenously supplied bacterial sphingomyelinase. Sphingomyelinase induced a dramatic change in the relative amounts of precursor and mature SREBP-1. As seen in FIGS. 2A–2B, a 2.5 fold increase in mature SREBP-1 levels was observed after 15 minutes treatment. Unlike TNF-α, the increase in mature SREBP-1 induced by sphingomyelinase persisted after 60 minutes. Sphingomyelinase was also capable of reducing the level of the precursor form of SREBP-1. See FIGS. 2A–B. Treatment with purified recombinant human sphingomyelinase produced similar results.

Much of the signal transducing ability of N-SMase has been ascribed to its ability to generate the lipid second messenger ceramide. Accordingly, the ability of a cell permeable ceramide analog $C_2$-ceramide (N-acetylsphingosine) was tested to induce SREBP-1 maturation. $C_2$-ceramide also induces SREBP-1 maturation in a sterol independent manner with greater magnitude than what was observed with either TNF-α or sphingomyelinase. $C_2$-ceramide increased the level of mature SREBP-14 fold after 30 minutes of treatment. See FIGS. 2A–2B. The persistent elevation of mature SREBP-1 levels observed with sphingomyelinase treatment also accompanied $C_2$-ceramide treatment. The increase in mature SREBP-1 is recapitulated with the addition of bovine brain ceramides but could not be induced with $C_2$-dihydroceramide, PL-$A_2$, or Phospholipid D treatment.

The kinetics of SREBP-1 maturation presented in this example would suggest that SREBP-1 proteolysis is a sufficiently early event to be involved in providing cholesterol to apoptotic cells. However, there was no evidence of apoptosis in the HH-25 human hepatocyte cell line used in this study. Without wishing to be bound to theory, it is conceivable that the sterol independent induction of SREBP-1 maturation in hepatocytes is a physiologic process that does not require that apoptosis be induced. Alternatively, the two pathways may diverge before the cell has been committed to apoptosis suggesting a manner in which sterol independent SREBP-1 proteolysis could be employed independent of the induction of apoptosis.

The sterol-independent cleavage of SREBP-1 observed with human hepatocytes could also occur by ceramide generated by the TNF-α induced N-SMase activation. This phenomenon may be reconstituted by the exogenous addition of N-SMase and/or $C_2$ ceramide to the hepatocytes.

Figures 1, 2C:
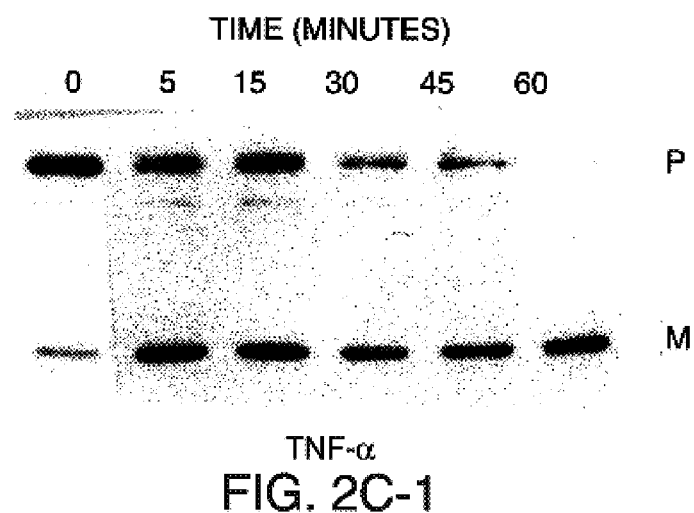
FIG. 2C is a representation of a Western immunoblot showing expression of TNF-$\alpha$, sphingomyelinase and $C_2$ ceramide.
Figures 2, 2C:
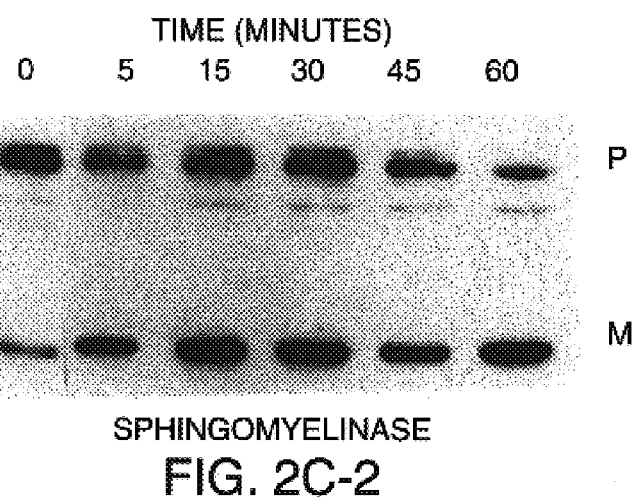
Figures 2, 2C, 3:
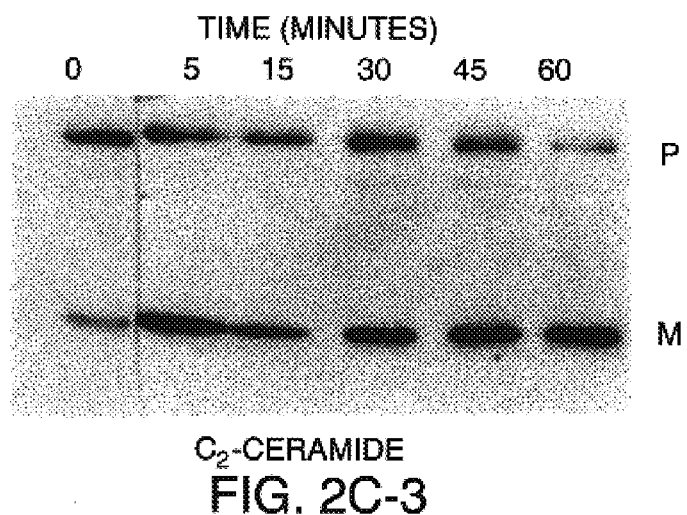

FIGS. 2A–2C illustrate effects of TNF-α sphingomyelinase and $C_2$-ceramide on the kinetics of SREBP-1 maturation—FIGS. 2A–2C is explained in more detail as follows: Cells were maintained in media supplemented with 1 μg/ml 25-hydroxy cholesterol and 15 μg/ml cholesterol for 24 hours before the experiment. The cells were treated for the indicated time as described in materials and methods. The cells were then harvested in PBS, pelleted and frozen. Lysis and nuclear fractionation were performed as described. Nuclear fractions (50 μg of protein) were electrophoresed on a 7.5% polyacrylamide gel and transferred to a PVDF membrane. Western blotting was performed as described. Band intensity was quantified via densitometry. Error bars represent ±one standard deviation from the mean. 2A) The kinetics of SREBP maturation as measured by the increase in mature SREBP-1 are plotted. Fold increase was calculated by comparing each time point to the corresponding control value (TNF-α is represented by stippled bars, bacterial sphingomyelinase is represented by light gray bars and $C_2$-ceramide by the dark bars.) 2B) Cells were treated with TNF-α (10 ng/ml) and prepared as described above. The bands corresponding to the precursor and mature forms of SREBP-1 were quantified and their ratio plotted. 2C) Representative Western blots from which numerical data was derived. Incubation time is indicated above and applies to all conditions. The membranes were exposed to film for 15 seconds. P and M denote the precursor and mature forms of SREBP-1 respectively.

EXAMPLE 3

Effects of TNF-α, Sphingomyelinase and $C_2$-ceramide on Apoptosis in Hepatocytes To demonstrate that the observed maturation of SREBP-1 was not an artifact of the more general phenomenon of apoptosis induced proteolysis we performed DNA laddering assays. The 160 bp DNA ladder characteristic of cells undergoing apoptosis was not observed in any of the samples.

TNF-α, $C_2$-ceramide and sphingomyelinase did not induce apoptosis demonstrating that in hepatocytes, SREBP-1 maturation is not part of the more general phenomenon of apoptotic protein hydrolysis.

EXAMPLE 4
Effects of TNF-α, Sphingomyelinase and $C_2$-ceramide Concentration on SREBP-1 Maturation The extent of TNF-α induced SREBP-1 maturation did not vary appreciably with concentration. A maximal effect was observed with 10 ng/ml of TNF-α. See FIGS. 3A–C. 250 milliunits of sphingomyelinase activity induced an 80% decrease in the precursor to mature ratio. As little as 1 μM of $C_2$-ceramide was effective in producing an 81% maximal effect. The maximal effect however, was obtained with a $C_2$-ceramide concentration of 50 M. See FIGS. 3A–C.

Figure 3A:
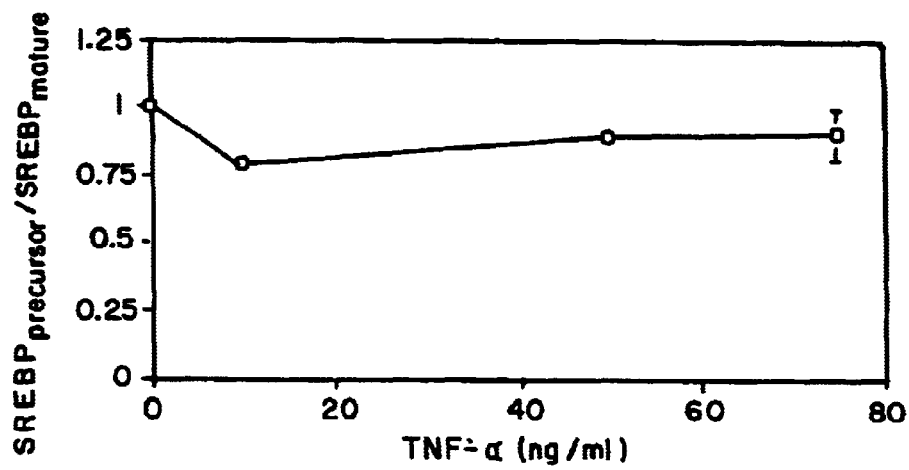
FIGS. 3A–C are graphs showing effects of TNF-$\alpha$ (3A), sphingomyelinase (3B), and $C_2$-ceramide (3C) on SREBP-1 maturation.
Figure 3B:
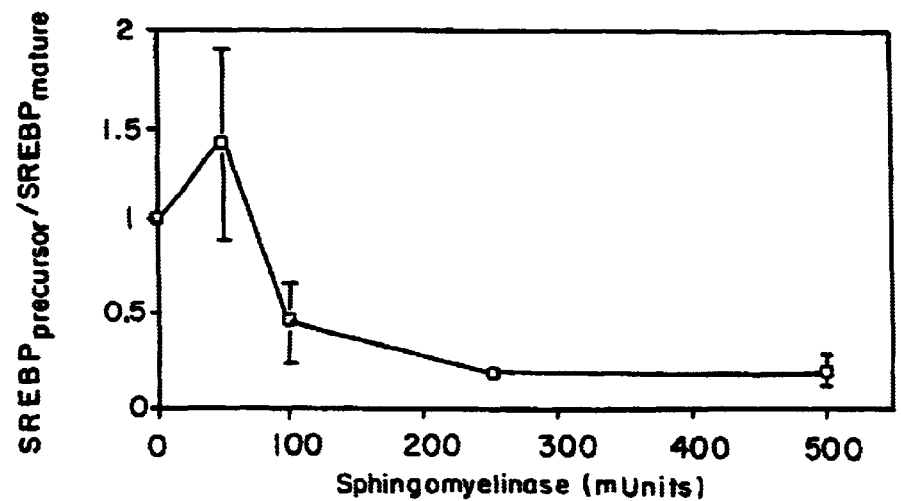
Figure 3C:
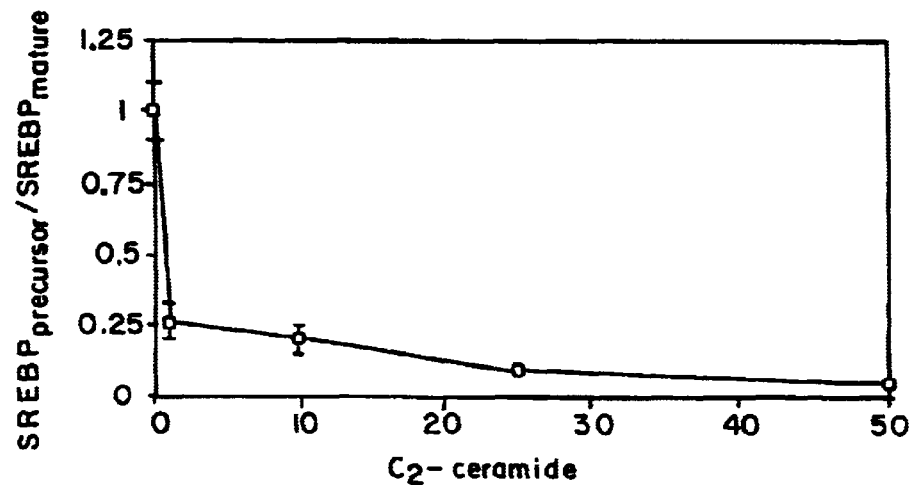

FIGS. 3A–3C show effects of TNF-α, sphingomyelinase and $C_2$-ceramide concentration on SREBP-1 maturation— The FIGS. 3A–3C are explained in more detail as follows. Cells were treated with either TNF-α, sphingomyelinase or $C_2$-ceramide at the indicated concentrations. Nuclear pellets were prepared and electrophoresed (50 μg of protein). The bands corresponding to the precursor and mature forms of SREBP-1 were quantified. The precursor to mature ratios were normalized to a single control to facilitate comparison. The control ratio was arbitrarily assigned a value of 1. A Unit of sphingomyelinase activity hydrolyzes 1.0 μmol of sphingomyelin per minute at 37° C. FIG. 3A (ng/ml TNF-α); FIG. 3B (mUnits of sphingomyelinase); FIG. 3C (micromolar C2-ceramide).

EXAMPLE 5
The Effect of Anti-N-SMase Antibodies on TNF-α Mediated SREBP-1 Maturation The availability of anti-N-SMase antibodies allowed us to examine the effects of TNF-α on this pathway independent of N-SMase activation (10). Polyclonal anti-N-SMase antibodies at a dilution of 1:200 completely block TNF-α induced SREBP-1 maturation. See FIG. 4. The suppression of TNF-α mediated SREBP-1 maturation was relieved with increasing antibody dilution. Preincubation with preimmune serum at the same dilution had no appreciable effect.

This example shows that pre incubation with anti-N-SMase antibody effectively blocked TNF-α induced SREBP-1 maturation. Inhibition was not observed with pre-immune serum treatment and was relieved with increasing antibody dilution. Such findings are confirmed by other studies such as those showing the ability of the antibody to inhibit TNF-α induced increases in cholesterol ester synthesis and N-SMase induced increases in $[^{125}I]$-LDL binding, internalization and degradation in human fibroblasts (15, 16).

Figure 4:
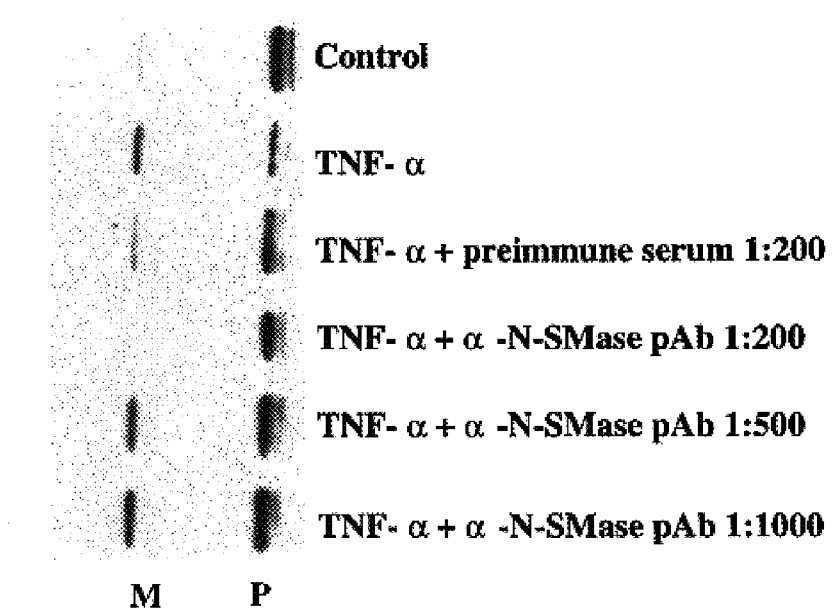
FIG. 4 is a representation of a Western immunoblot showing effect of anti-N-SMase antibodies on TNF-$\alpha$-induced SREBP-1 maturation.

FIG. 4 shows effect of anti-N-SMase antibodies on TNF-α induced SREBP-1 maturation. The FIG. 4 is explained in more detail as follows. Cells were maintained in media supplemented with 1 μg/ml 25-hydroxycholesterol and 15 g/ml cholesterol for 24 hours before the experiment. The cells were switched to serum free media for 15 minutes and then incubated with anti-N-SMase antibodies or rabbit preimmune serum at the indicated dilution for 30 minutes prior to TNF-α addition (10 ng/ml). The cells were then harvested, pelleted and lysed as described. The samples were electrophoresed on a 7.5% polyacrylamide gel and transferred to a PVDF membrane. Bands were visualized as described. Film was exposed for 15 seconds.

EXAMPLE 6
Effects of TNF-α, $C_2$-ceramide and Sphingomyelinase on the Subcellular Localization of SREBP-1

To determine if the SREBP-1 fragment generated by TNF-α, $C_2$-ceramide or sphingomyelinase treatment was capable of nuclear translocation, immunofluorescence studies were pursued. Previous immunofluorescence studies have relied on the overexpression of precursor and mature forms of SREBP-1 (14). We were able to visualize endogenous SREBP-1 in treated and untreated cells with polyclonal antibodies directed against the DNA binding domain of SREBP-1. Since the DNA binding domain is common to both the precursor and mature forms, examination of the total distribution of endogenous SREBP-1 was possible.

TNF-α, $C_2$-ceramide and sphingomyelinase all are capable of inducing changes in the subcellular localization of SREBP-1. See FIG. 5A. Untreated cells display an even staining pattern throughout their cell bodies. This is consistent with the localization of precursor SREBP-1 to intracellular membranes (14). However, cells treated with TNF-α, $C_2$-ceramide or sphingomyelinase all exhibit intense nuclear staining and little extra-nuclear staining. See FIGS. 5B–5D. The rapid change in the subcellular localization of SREBP-1 is consistent with a precursor/product relationship between the two forms and provides additional evidence that the mature SREBP-1 fragment generated by treatment is capable of nuclear translocation.

Figure 5A:
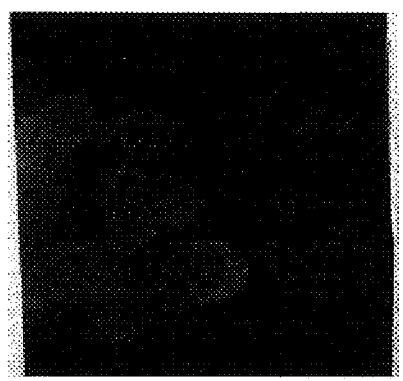
FIGS. 5A–D are representations of indirect immunofluorescence micrographs showing SREBP-1 expression in cells.
Figure 5B:
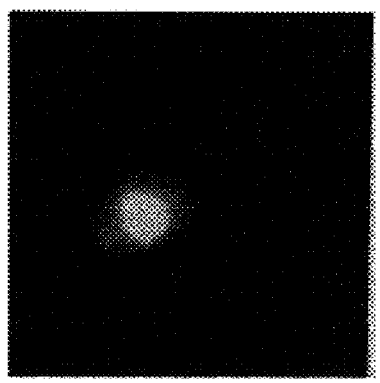
Figure 5C:
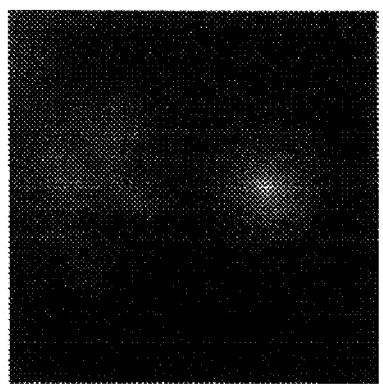
Figure 5D:
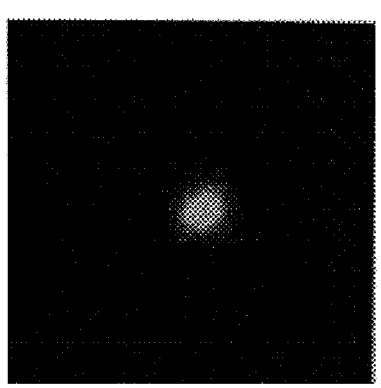

FIGS. 5A–5D show indirect immunofluorescence of SREBP-1. FIGS. 5A–5D are discussed in more detail as follows. SREBP-1 was visualized with rabbit polyclonal antibodies directed towards the N-terminal DNA binding domain which is common to both the precursor and mature forms. Cells were maintained in media supplemented with 1 μg/ml 25-hydroxycholesterol and 15 μg/ml cholesterol for 24 hours before the experiment. Immunofluorescence was performed as described. All magnifications are 40× and all photographs were taken of samples that were fixed 30 minutes after initiating treatment. FIG. 5A) Control cells, FIG. 5B) Cells treated with TNF-α (10 ng/ml), FIG. 5C) Cells treated with sphingomyelinase (100 mUnits), FIG. 5D) Cells treated with $C_2$-ceramide (10 μM).

EXAMPLE 7
Electrophoretic Mobility Shift Assays

Electrophoretic mobility shift assays were pursued to demonstrate that the mature SREBP-1 fragment is additionally capable of binding to its consensus sequence. The amount of electrophoretically retarded probe increases with time following TNF-α treatment. See FIG. 6A. The kinetics of this process is consistent with the activation of N-SMase. The amount of probe bound increases with sphingomyelinase and ceramide treatment. As expected, $C_2$-ceramide induces a more rapid accumulation of active, nuclear SREBP-1 than either TNF-α or sphingomyelinase. See FIGS. 6A–6C. Antibodies directed towards the DNA binding domain of SREBP successfully compete with the oligonucleotide probe for binding. See FIG. 6D. Binding of the probe is not titrated by an unrelated oligonucleotide but is decreased with the addition of a non-radioactive competing probe.

Figure 6A:
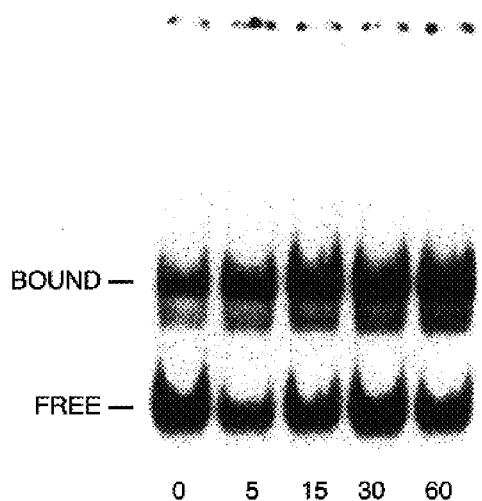
Figure 6B:
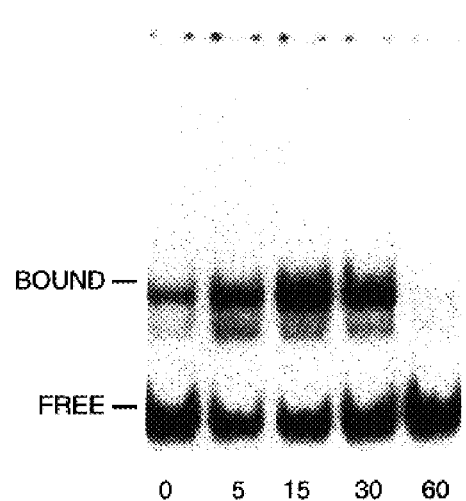

FIGS. 6A–6D show electrophoretic mobility shift assays. FIGS. 6A–D are explained in more detail as follows. Cells were maintained in sterol supplemented media. Nuclear pellets were prepared and assayed as described in materials and methods. Probe that has been bound by mature SREBP-1 is indicated as "Bound". Unbound probe is indicated as "Free". The kinetics (in minutes) of SREBP-1 binding to the probe in response to treatment with (FIG. 6A). TNF-α (10 ng/ml), (FIG. 6B) sphingomyelinase (100 mUnits) and (FIG. 6C) $C_2$-ceramide (10 M). (FIG. 6D). The cells were treated with either TNF-α (10 ng/ml), sphingomyelinase (100 mUnits) or $C_2$-ceramide (10 μM) for 15 minutes. Supershift assays were then performed with antibodies raised against the DNA binding domain of SREBP-1. The presence or absence of antibody is indicated by (+) and (−) respectively. Pre-immune IgG was used as a control.

The gel mobility shift experiments in FIGS. 6A–D clearly indicate that TNF-α, N-SMase and $C_2$ ceramide all induce SREBP-1 levels in hepatocytes. It is known that TNF-α induces sterol metabolism in cultured human fibroblasts (15) and LDL receptors (16, 17). The present data indicate that indeed TNF-α induces LDL receptor mRNA level in human hepatocytes. One result is that TNF-α induced increase in mature SREBP-1 level is accompanied by increased LDL receptors and sterol metabolism.

EXAMPLE 8

Effects of Overexpression of Neutral Sphingomyelinase (N-SMase) and Recombinant N-SMase on the Maturation of Sterol-regulatory Element Binding Protein-1 and Low Density Lipoprotein Receptor Expression in Cultured Human Hepatocytes The present example was conducted to address whether the overexpression of N-SMase employing two separate N-SMase plasmid DNA(PHH-1, representing the entire nucleotide sequence in N-SMase cDNA and PHH-11, representing nucleotide sequence 862–1414) would increase the maturation of SREBP-1 and LDL receptor mRNA expression in a human hepatocyte cell line HH-11. Cells transfected with mock plasmid cDNA(PSV-SPOT) served as a control and cells incubated with C-2 ceramide previously shown to induce SREBP-1 maturation served as a positive control.

Briefly, human hepatocytes($1 \times 10^4$) were seeded in sterile 100 mm² in medium containing 10% dialyzed, heat inactivated fetal bovine serum without antibiotics. Twenty four hours later medium was replaced with 9 ml of fresh serum free medium. After incubation for 30 min at 37° C. 5–40 μg of the plasmid DNA in 1 ml of a $CaCl_2$ solution (mixed with equal volume of 0.25–2.5 M $CaCl_2$ solution in HEPES buffer and HEPES buffer pH 6.95). Following gentle mixing incubation of cells was continued for 5–24 hr at 37° C. The transfection reaction was terminated by removing the medium and washing the cells with serum free medium. Next, fresh serum supplemented medium was added and incubation was continued for an additional 24 hr and cells were harvested in appropriate buffer centrifuged and stored frozen until further analysis. Cell pellets were homogenized and suitable aliquots subjected to Western immunoblot analysis as described below and in Examples 1–7 above. Total RNA was isolated from another batch of cells transfected as above and subjected to Northern analysis employing a $^{32}P$ labeled LDL receptor consensus sequence. The autoradiographs were developed and photographed.

Cells transfected with 0.2 μg/ml of PHH1 or PHH11 showed a 2-fold increase in N-SMase activity compared to mock cDNA transfected cells. This was accompanied with aPHH1 and PHH11 concentration dependent increase in the maturation of SREBP-1 in human hepatocytes. See FIG. 7. As shown in lanes 3–6 transfection of cells with 5,10,20,40 μg of PHH1 plasmid DNA/dish resulted in a gradual but marked increase in the maturation of SREBP-1 as compared to mock cDNA transfected cells (lane1, FIG. 7). In contrast, a marked increase in the maturation of SREBP-1 was noted in cells transfected with 20 μg/dish of PHH11 plasmid DNA (lane 9 FIG. 7) but subsided at a higher concentration. As expected form the Examples 1–7 above, cells incubated with C-2 ceramide (μM) markedly increased the maturation of SREBP-1(lane 2 FIG. 7). In additional experiments we observed that increasing the time of transfection from 8 hr to 24 hr decreased the maturation of SREBP-1 in hepatocytes. Moreover, decreasing the concentration of $CaCl_2$ from 2.5M to 0.25M was ineffective.

Figure 8:
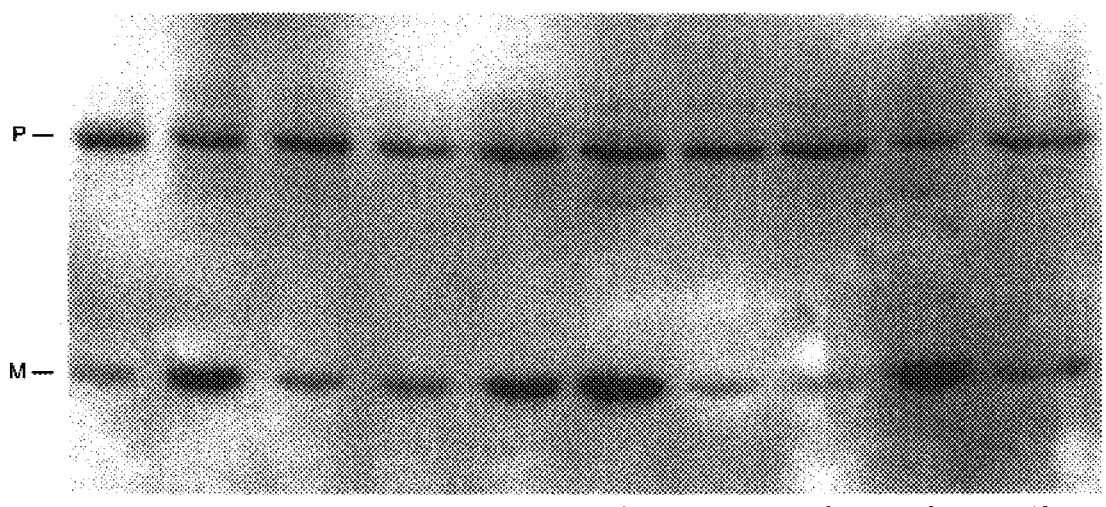
FIG. 8 is a representation of a Western immunoblot showing N-SMase protein in cells expressing increasing amounts of a recombinant vector encoding the N-SMase (PHH1 lanes 3–6; PHH11 lane 9).

Northern gel analysis revealed that transfection with PHH1 and PHH11(lanes 2, 3, respectively in FIG. 8) significantly increased the level of LDL receptor mRNA as compared to cells transfected with mock cDNA (lane 1 FIG. 8).

Figure 9:
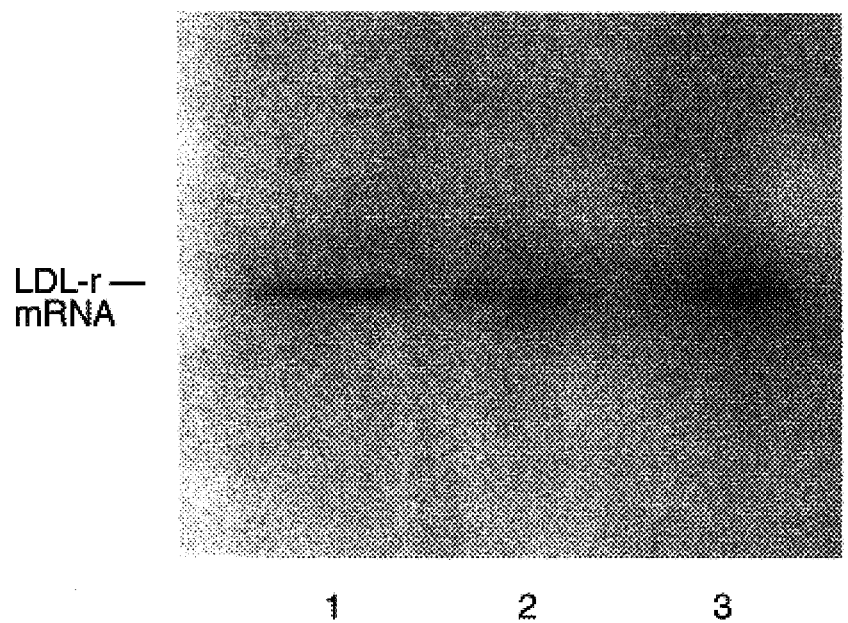
FIG. 9 is a representation of a Northern blot showing expression of the vectors encoding the N-SMase protein (lane 2 PHH1; lane 3 PHH11).
Figure 10:
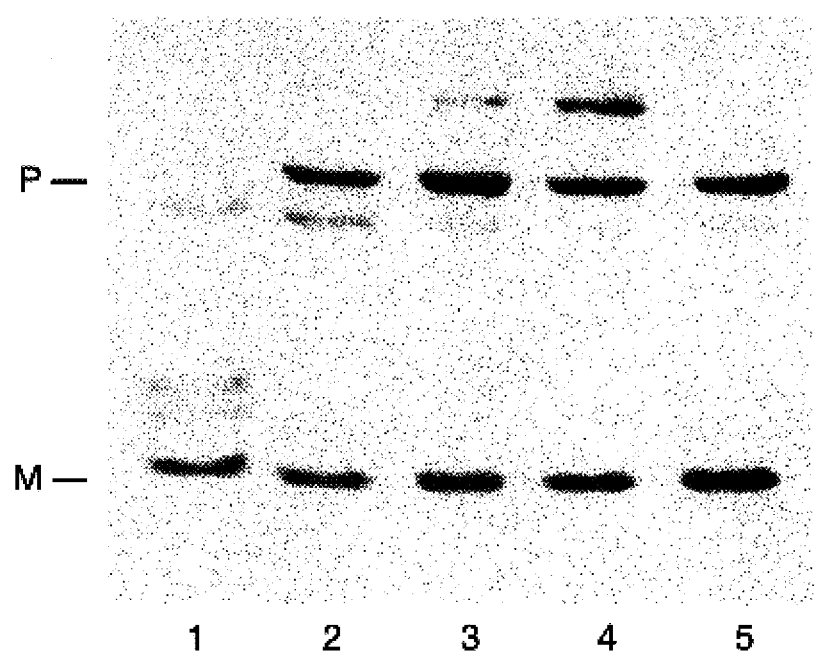
FIG. 10 is a representation of a Western immunoblot illustrating SREBP-1 expression and maturation in cells.

In another experiment hepatocytes were incubated with purified bacterial recombinant N-SMase. Preferred methods of making and using the recombinant N-SMase are described in the co-pending U.S. patent application Ser. No. 08/774,104, now issued as U.S. Pat. No. 5,919,687. That N-SMase was subjected to western immunoblot analysis employing antibody against SREBP-1. As shown in FIG. 9, cells incubated with C-2 ceramide markedly increased the maturation of SREBP-1 (lane1). In comparison the r-N-SMase exerted a concentration-dependent increase in the maturation of SREBP-1 (lane 2, 3, 4, 5 representing 0.4, 0.8, 2, and 4 μg/ml of r-N-SMase, respectively).

This example shows that overexpression of N-SMase or feeding r-N-SMase to hepatocytes stimulates the maturation of SREBP-1 and consequently an increase in the LDL receptor mRNA levels.

The Examples 1–8 above highlight a novel pathway by which SREBP-1 maturation could be effected in a sterol independent manner. It was found that TNF-α is capable of inducing SREBP-1 maturation in a sterol independent manner in human hepatocytes. These findings are not a general response to growth factors, as they could not be recapitulated with EGF or PDGF. The maturation, nuclear translocation, and SRE binding activity of SREBP-1 in response to TNF-α closely paralleled the kinetics of N-SMase activation. The effect of TNF-α on SREBP-1 maturation could be reconstituted with exogenously supplied bacterial or human sphingomyelinase $C_2$-ceramide but could not be recapitulated with dihydroceramide, PL-$A_2$, or PL-D.

In particular, Examples 1–7 show that addition of $C_2$-ceramide, a water soluble ceramide analog, or bacterial sphingomyelinase mimicked the effect of TNF-α on SREBP-1 maturation. $C_2$-ceramide and sphingomyelinase induced more extensive SREBP-1 maturation than TNF-α. Without wishing to be bound to theory, this observation may reflect the presence of a regulatory event upstream of ceramide generation that is effectively bypassed with exogenous ceramide or sphingomyelinase. Also, the lack of apparent dose dependence observed with TNF-α treatment might be attributable to saturable binding of the TNF-α receptors or an internal regulatory event that reduces the signaling capacity of the TNF-α receptors.

The present data and discussion indicate a model in which TNF-α initiates SREBP-1 proteolysis. The model (FIG. 7) in which there is shown TNF-α binding to one or more of its cell surface receptors and in so doing promotes the activation of N-SMase. N-SMase hydrolyzes membrane sphingomyelin into ceramide and phosphocholine. Ceramide, in turn, activates a protease perhaps CPP32 that mediates SREBP-1 maturation. According to the model, the mature SREBP-1 then migrates into the nucleus as shown and drives the transcription of genes with an upstream sterol regulatory element.

The model illustrated in FIG. 7 clarifies how sterol homeostasis can occur in the presence of increased cytosolic sterols, which would be predicted to suppress SREBP-1 maturation. One advantage conferred by the participation of neutral sphingomyelinase in cholesterol homeostasis is that it is capable of providing a short term solution to cholesterol starvation through mobilization of plasma membrane cholesterol and can facilitate long term compensatory mechanisms by promoting the maturation of SREBP-1.

The model shown in FIG. 7 also shows that TNF-α is capable of inducing SREBP-1 proteolysis independent of the presence of sterols. Exogenously supplied sphingomyelinase and ceramide are also capable of inducing SREBP-1 proteolysis in a time and dose dependent manner. The kinetics of SREBP-1 maturation is consistent with the activation of neutral sphingomyelinase by TNF-α. Furthermore, recombinant human N-SMase can also exert a time and concentration dependent induction of SREBP-1 maturation. In addition, anti-N-SMase antibodies block SREBP-1 maturation. These findings indicate that neutral sphingomyelinase is necessary for TNF-α induced, sterol independent SREBP-1 cleavage.

The present examples and discussion identify N-SMase in the TNF-α initiated signal transduction pathway leading to SREBP-1 maturation and provide evidence that ceramide is the second messenger employed. Also shown is an important role for TNF-α in the regulation of cholesterol homeostasis.

The present findings are summarized as follows. The role of TNF-α as a mediator of SREBP-1 maturation was investigated in human hepatocytes.

One significant aspect of the above Examples and discussion is that ceramide stimulated SREBP-1 maturation even in the presence of cholesterol and 25-hydroxycholesterol both of which are known suppressers of SREBP-1 maturation. This indicates that ceramide mediated maturation of SREBP-1 maturation is a novel, sterol independent mechanism by which cholesterol homeostasis may be regulated.

The following materials and methods were used as needed in the above Examples 1–8.

1. Materials—A continuous line of human hepatocytes designated HH-25 were prepared from normal human tissue (18). Alpha modified minimal essential medium was purchased from Mediatech (Herndon, Va.). Fetal bovine serum was purchased from Hyclone, Salt Lake City, Utah. F10 media and the insulin-transferrin-selenium supplement were purchased from Gibco-BRL (Gaithersburg, Md.). Human recombinant EGF, PDGF and TNF-α were from Upstate Biotechnology (Lake Placid, N.Y.). $C_2$-ceramide (N-acetylsphingosine) was obtained from Matreya (Pleasant Gap, Pa.). [$^{14}$C]-sphingomyelin (specific activity 50 mCi/mmol) was from American Radiolabeled Chemicals (St. Louis, Mo.). Anti-SREBP-1 antibody was purchased from Santa Cruz Biotechnology (Santa Cruz, Calif.). Sphingomyelinase from Streptomyces species and all other redrugs were obtained from Sigma.

2. Cell Culture

HH-25 cells were grown in alpha-minimal essential media supplemented with 100 units/ml penicillin, 100 g/ml streptomycin, 10 g/ml insulin, 0.1 μM selenium, 5.5 μg/ml transferrin, 0.5 μg/ml linoleic acid and 10% fetal bovine serum (media A). The cells were incubated in serum free F10 media for 30 to 60 minutes prior to initiating treatment with TNF-α, $C_2$-ceramide or sphingomyelinase.

3. Cell Fractionation

Following treatment, the cells were washed with 5 ml of PBS and pelleted at 1500×g for 10 minutes at 4° C. The pellet was stored at −70° C. and lysed in 0.5 ml buffer A (10 mM HEPES pH 7.4, 5 mM EDTA, 0.25 mM EGTA, 50 mM NaF, 7 mM β-mercaptoethanol, 0.35M sucrose, 0.1% NP-40 and protease inhibitors 1 mM PMSF, 2 μg/ml aprotinin, 10 μg/ml leupeptin and 5 μg/ml pepstatin). The lysate was centrifuged at 12,000×g for 15 minutes at 4° C. to prepare a nuclear fraction. The protein concentration of these samples was determined by the method of Lowry et al. al. (19).

4. Neutral Sphingomyelinase Assay

After stimulation with TNF-α for the indicated time intervals, the cells were washed once with 5 ml PBS and harvested. The pellet was stored frozen at −70° C. and resuspended in 0.5 ml buffer B (100 mM Tris HCl pH 7.4, 0.1% triton X-100, 1 mM EDTA and protease inhibitors). The cell suspension was sonicated 3 times (3 second bursts) using a probe sonicator and centrifuged at 500×g at 4° C. for 5 minutes. The supernatant was used as the enzyme source.

100 μg of protein was assayed for neutral sphingomyelinase activity in a buffer consisting of 5 mM Tris HCl pH 7.4, 0.1% triton X-100, 0.1 mg BSA, 5 mM $MgCl_2$, and 50 moles [$^{14}$C] sphingomyelin (12,000 dpm). The assay was incubated at 37° C. for 1.5 hours and terminated with the addition of 1 ml of 10% TCA. The precipitate was pelleted (1000×g at 4° C. for 20 minutes) and 1 ml of the supernatant was extracted with 1 ml anhydrous diethyl ether. 0.5 ml of the aqueous phase was removed for liquid scintillation counting.

5. Immunoblotting

50 μg of nuclear protein was separated by gel electrophoresis on a 7.5% polyacrylamide gel. Gels were calibrated by high range molecular weight markers (Bio-Rad product #161-0303, New York, N.Y.) which were transferred to a polyvinyl difluoride (PVDF) membrane and visualized with coomassie staining. Rabbit polyclonal antibodies against SREBP-1 were used at 0.5 μg/ml according to the instructions of the manufacturer. The antibody was visualized with horseradish peroxidase conjugated anti-rabbit IgG made in donkey (Amersham) using the Enhanced Chemiluminescence (ECL) Western Blotting Detection System Kit (Amersham). PVDF membranes were exposed to Hyperfilm ECL (Amersham) for the indicated time. Immunoblots were quantified via densitometry performed on a PDI densitometer scanner (model 20J7) coupled to a SPARC IRC workstation.

5. Indirect Immunofluorescence

Cultured HH-25 cells were grown on coverslips and treated as described. After treatment, the cells were washed 3×5 minutes with PBS containing 1 mM $MgCl_2$ and 0.1 mM $CaCl_2$ (solution A). The cells were fixed with 3% paraformaldehyde in solution A for 10 minutes and permeabilized with 0.5% Triton X-100 in solution A for 6 minutes at room temperature. The coverslips were then washed 3×5 minutes with solution A.

Primary antibody (anti-SREBP1) was used at a dilution of 0.5 g/ml in PBS and applied for 1 hour with gentle shaking. The cells were washed as above and a FITC conjugated anti-rabbit IgG secondary antibody, was applied for ½ hour according to the instructions of the manufacturer. The coverslips were washed, mounted on microscope slides and were viewed and photographed at the indicated magnification on a Zeiss Axiovert 25 fluorescence microscope.

6. DNA Laddering Assay

Cells were treated with either TNF-α, sphingomyelinase or $C_2$-ceramide for 1 hour at concentrations identical to those used in the SREBP-1 maturation studies. The cells were then washed twice with minimal essential medium and refed with media A for 6 hours. The cells were harvested and genomic DNA was prepared as described (22). Genomic DNA was electrophoresed and stained with ethidium bromide.

7. Electrophoretic Mobility Shift Assays

Gel mobility shift assays were performed as follows. Each 20 μl reaction mixture contained 8–10 μg of nuclear protein plus a α-[$^{32}$P]-labeled 25-base pair oligonucleotide probe containing the SREBP-binding site (14) in binding buffer (10 mM Hepes, pH 7.5, 0.5 mM spermidine, 0.15 mM EDTA, 10 mM dithiothreitol, 0.35 mM sucrose). The reaction mixture was incubated at room temperature for 15 min and loaded directly onto a 6.5% polyacrylamide (49:0.6 acrylamide/bisacrylamide) gel in a buffer of 25 mM Tris borate (pH 8.0), 0.25 mM EDTA. In some experiments, antisera specific for SREBP or preimmune sera were added to reaction mixtures to determine the composition of protein-probe complexes. For these "supershift" assays, extracts were incubated with 1 µl of preimmune sera or an equal volume of anti-SREBP antisera at 4° C. for 30 min prior to addition of α-[$^{32}$P]-labeled probe. In all experiments, proteins were separated by electrophoresis at 200 V for 2 h at room temperature. Gels were dried and exposed to Kodak XAR film with intensifying screens. Assays were repeated with nuclear extracts obtained from three unique experiments and evaluated by phosphoimage analysis to ensure reproducibility of results.

REFERENCES

1) Goeddel, D. V., Aggarwal, B. B., Gray, P. W., Leung, D. W., Nedwin, G. E., Palladino, M. A., Patton, J. S., Pennica, D., Shepard, H. M., Sugarman, B. J. and Wong, G. H. W. (1986) *Cold Spring Harbor Symp. Quant. Biol.* 51, 597–609.
2) Baringa, M., (1996) *Science* 273, 735–737. Bazzoni, F. and Beutler, B. (1996) *NEJM* 334, 1717–1725
3) Chatterjee, S., (1993) *Adv. Lipid Res.* 26, 25–48.
4) Tepper, C. G., Jayadev, S., Liu, B.,Bielawska, A., Wolff, R., Yonehara, S., Hannun, Y. A., and Seldin, M. F. (1995) *Proc. Natl. Acad. Sci. U.S.A.* 92, 8443–8447.
5) Cifone, M. G., DeMaria, R., Roncaioli, P., Rippo, M. R. Azuma, M. Lanier, L. L., Santoni, A., and Testi, R. (1994) *J. Exp. Med.* 180, 1547–1552.
6) Okazaki, T., Bell, R. M., and Hannun, Y. A. (1995) *J. Biol. Chem.* 264, 19076–19080.
7) Mathias, S., Younes, A., Kan, C. C., Orlow, I., Joseph, C., and Kolesnick, R. N., (1993) *Science* 259, 519–522.
8) Dobrowsky, R. T., Werner, M. H., Castellino, A. M., Chao, M. V. and Hannun, Y. A. (1994) *Science* 265, 1596–1599.
9) Chan, C. G., and Ochi, A. (1995) *Eur. J. Immunol.* 25, 1999–2004.
10) Kim, M. Y., Linardic, C., and Hannun, Y. A. (1991) *J. Biol. Chem.* 266, 484–489.
11) Cuvillier, O., Pirianov, G., Kleuser, B., Vanek, P. G., Coso, O. A., Gutkind, J. S., and Spiegel, S., *Nature* 381, 800–803.
12) Goldstein, J. L., and Brown, M. S. (1986) *Nature* 343, 425–430.
13) Dawson, P. A., Hofmann, S. L., van der Westhhuyzen, D. R., Brown, M. S., and Goldstein, J. L. (1988) *J. Biol. Chem.* 263, 3372–3379.
14) Wang, X., Sato, R., Brown, M. S., and Goldstein, J. L. (1994) *Cell* 77, 53–62.
15) Chatterjee, S., (1994) *J. Biol. Chem.* 269, 879–882.
16) Chatterjee, S. (1993) *J. Biol. Chem.* 268, 3401–3406.
17) Hamanaka, R., Kohno, K., Seguchi, T., Okamura, K., Morimoto, A., Ono, M., Ogata, J., and Kuwano, M. (1992) *J. Biol. Chem.* 267, 13160–13165.
18) Wang, X., Zelenski, N. G., Yang, J., Sakai, J., Brown, M. S., and Goldstein, J. L. (1996) *EMBO* 15, 1012–1020.
19) Mizushima, N., Koike, R., Kohsaka, H., Kushi, Y., Handa, S., Yagita, H., Miyasaka N. (1996) *FEBS Lett.* 395, 267–271.
20) Bittman, R., Kasireddy, C. R., Mattjus, P., and Slotte, J. P. (1994) *Biochemistry* 33, 11776–11781.
21) Kan, C., Ruan, Z., and Bittman, R., (1991) *Biochemistry* 30, 10746–10754.
22) Clejan, S., and Bittman, R., (1984) *J. Biol. Chem.* 259, 10823–10826.
23) Adam-Klages, S., Adam, D., Weigmann, K., Struve, S., Kolanus, W., Schneider-Mergener, J., and Kronke, M. (1996) *Cell,* 86, 937–947.
24) Lawler, F. J. et al. (1998) *J. Biol. Chem.* 273: 5058.
25) Shimomura, I., et al. (1998) *J. Biol. Chem.* 273: 35299.
26) Brown, M. S. and J. L. Goldstein (1997) *Cell* 89: 331.

The invention has been described with reference to preferred embodiments thereof. However, it will be appreciated that those skilled in the art, upon consideration of this disclosure, may make modifications and improvements within the spirit and scope of the invention.

What is claimed is:

1. A method for modulating serum cholesterol level in a mammal, wherein the method comprises administering to the mammal a therapeutically effective amount of an anti-lipemic drug comprising at least one effector of the sterol regulatory element binding protein 1 (SREBP-1) and at least one identified serum cholesterol inhibitor, wherein the SREBP-1 effector is a sphingolipid.

2. The method of claim 1, wherein the spingolipid is ceramide.

3. The method of claim 1, wherein each of the methods reduces serum cholesterol levels in the mammal by at least 20% when compared to a control mammal as determined by a standard serum cholesterol assay.

4. The method of claim 2, wherein the sphingolipid is a C-2, C-4, C-6 or C-8 ceramide.

5. The method of claim 1, wherein the serum cholesterol inhibitor is one of fluvastatin, simvastatin, lovastatin, pravastatin, mevinolin (compactin), atorvastatin; or a clinically acceptable derivative thereof.

6. The method of claim 1, wherein the sphingolipid is attached to the serum cholesterol inhibitor by at least one covalent bond.

7. The method of claim 6, wherein the serum cholesterol inhibitor is one of fluvastatin, simvastatin, lovastatin, pravastatin, mevinolin (compactin), atorvastatin; or a clinically acceptable derivative thereof; and the sphingolipid is ceramide, and further wherein the ceramide is covalently linked to a reactive hydroxyl group on the serum cholesterol inhibitor.

8. The method of claim 7, wherein the reactive hydroxyl group of the serum cholesterol inhibitor is covalently linked to the C-3 carbon of the ceramide.

9. The method of claim 1, wherein the anti-lipemic drug further includes a bifunctional spacer covalently linked between the effector of the sterol regulatory element binding protein 1 (SREBP-1) and the serum cholesterol inhibitor.

10. The method of claim 1, wherein the anti-lipemic drug comprises covalently linked in sequence: 1) ceramide, 2) a heterobifunctional spacer group linked to the C-3 group of the ceramide, and 3) the hydroxyl (—OH) group of the fluvastatin, simvastatin, lovastatin, pravastatin, mevinolin (compactin), atorvastatin; or derivative thereof linked to a reactive carbon atom on the heterobifunctional spacer.

11. The method of claim 1, wherein the anti-lipemic drug comprises a sphingolipid associated with an inhibitor of HMG CoA reductase or HMG CoA synthetase.

12. The method of claim 1, wherein the mammal is a human subject that has or is suspected of having a high risk cholesterol level.

* * * * *